United States Patent
Schena et al.

(10) Patent No.: US 10,973,598 B2
(45) Date of Patent: Apr. 13, 2021

(54) REDUNDANT AXIS AND DEGREE OF FREEDOM FOR HARDWARE-CONSTRAINED REMOTE CENTER ROBOTIC MANIPULATOR

(71) Applicant: Intuitive Surgical Operations, Inc., Sunnyvale, CA (US)

(72) Inventors: Bruce Michael Schena, Menlo Park, CA (US); Roman L. Devengenzo, San Jose, CA (US); Gary C. Ettinger, Cupertino, CA (US); Eugene F. Duval, Menlo Park, CA (US); Nicola Diolaiti, Menlo Park, CA (US); Daniel H. Gomez, Sunnyvale, CA (US)

(73) Assignee: Intuitive Surgical Operations, Inc., Sunnyvale, CA (US)

(*) Notice: Subject to any disclaimer, the term of this patent is extended or adjusted under 35 U.S.C. 154(b) by 106 days.

(21) Appl. No.: 16/178,242

(22) Filed: Nov. 1, 2018

(65) Prior Publication Data
US 2019/0069965 A1    Mar. 7, 2019

Related U.S. Application Data

(63) Continuation of application No. 15/058,914, filed on Mar. 2, 2016, now Pat. No. 10,143,525, which is a (Continued)

(51) Int. Cl.
*A61B 34/37* (2016.01)
*A61B 34/30* (2016.01)
(Continued)

(52) U.S. Cl.
CPC ............. *A61B 34/37* (2016.02); *A61B 34/30* (2016.02); *A61B 34/70* (2016.02); *A61B 2017/00477* (2013.01); *A61B 2034/305* (2016.02)

(58) Field of Classification Search
CPC ......... A61B 34/37; A61B 34/72; A61B 34/71; A61B 34/70; A61B 34/30; A61B 2017/00477; A61B 2034/305
See application file for complete search history.

(56) References Cited

U.S. PATENT DOCUMENTS

| 5,397,323 A | 3/1995 | Taylor et al. |
| 5,445,166 A | 8/1995 | Taylor |

(Continued)

FOREIGN PATENT DOCUMENTS

| CN | 1642696 A | 7/2005 |
| CN | 101304701 A | 11/2008 |

(Continued)

OTHER PUBLICATIONS

Extended European Search Report for Application No. EP13798213, dated Dec. 22, 2015, 7 pages.

(Continued)

*Primary Examiner* — Erich G Herbermann
(74) *Attorney, Agent, or Firm* — Kilpatrick Townsend & Stockton LLP

(57) ABSTRACT

A manipulator for articulating a surgical tool during surgery includes an instrument holder, a parallelogram linkage assembly, an offset extension link, a yaw joint, and a mounting base. The instrument holder is configured to couple with the surgical tool. The parallelogram linkage assembly produces motion of the instrument holder that is limited to rotation about a pitch axis that intersects a remote center of manipulation. The offset extension link has an offset extension link distal end and an offset extension link proximal end. The yaw joint is connected to the offset extension link proximal end and produces motion of the instrument holder that is limited to rotation about a yaw axis that intersects the remote center of manipulation. The offset (Continued)

extension link distal end is offset from the yaw axis. The mounting base is coupled with the yaw joint.

9 Claims, 19 Drawing Sheets

Related U.S. Application Data continuation of application No. 13/906,888, filed on May 31, 2013, now Pat. No. 9,295,524.

(60) Provisional application No. 61/654,414, filed on Jun. 1, 2012.

(51) Int. Cl.
*A61B 34/00* (2016.01)
*A61B 17/00* (2006.01)

(56) References Cited

U.S. PATENT DOCUMENTS

| | | |
|---|---|---|
| 5,855,553 A | 1/1999 | Tajima et al. |
| 6,246,200 B1 | 6/2001 | Blumenkranz et al. |
| 6,451,027 B1 | 9/2002 | Cooper et al. |
| 6,788,018 B1 | 9/2004 | Blumenkranz |
| 7,386,365 B2 | 6/2008 | Nixon |
| 7,763,015 B2 | 7/2010 | Cooper et al. |
| 8,004,229 B2 | 8/2011 | Nowlin et al. |
| 8,162,926 B2 | 4/2012 | Schena |
| 8,989,903 B2 | 3/2015 | Weir et al. |
| 9,084,613 B2 | 7/2015 | Qutub |
| 9,295,524 B2 | 3/2016 | Schena et al. |
| 9,517,106 B2 | 12/2016 | Hourtash et al. |
| 9,730,611 B2 | 8/2017 | Kowshik et al. |
| 9,883,818 B2 | 2/2018 | Weber et al. |
| 9,931,170 B2 | 4/2018 | Auld |
| 9,943,372 B2 | 4/2018 | Sholev et al. |
| 9,949,802 B2 | 4/2018 | Cooper et al. |
| 10,011,018 B2 | 7/2018 | Mcgrogan et al. |
| 10,022,067 B2 | 7/2018 | Kowshik et al. |
| 10,143,525 B2 | 12/2018 | Schena et al. |
| 2003/0208189 A1 | 11/2003 | Payman |
| 2003/0221504 A1 | 12/2003 | Stoianovici et al. |
| 2004/0024387 A1 | 2/2004 | Payandeh et al. |
| 2007/0173975 A1 | 7/2007 | Schena |
| 2007/0173977 A1 | 7/2007 | Schena |
| 2009/0041565 A1 | 2/2009 | Rodriguez |
| 2009/0234369 A1 | 9/2009 | Bax et al. |
| 2009/0292299 A1* | 11/2009 | Cooper .................. A61B 34/37 606/130 |
| 2010/0224022 A1 | 9/2010 | Choi et al. |
| 2010/0240989 A1 | 9/2010 | Stoianovici et al. |
| 2011/0257786 A1 | 10/2011 | Caron et al. |
| 2011/0277775 A1 | 11/2011 | Holop et al. |
| 2012/0124824 A1 | 5/2012 | Burbank et al. |
| 2012/0132018 A1 | 5/2012 | Tang et al. |
| 2013/0178868 A1 | 7/2013 | Roh |
| 2013/0282021 A1 | 10/2013 | Parihar |
| 2013/0338679 A1 | 12/2013 | Rosielle et al. |
| 2014/0180309 A1 | 6/2014 | Seeber et al. |
| 2014/0336669 A1 | 11/2014 | Park |
| 2015/0157411 A1 | 6/2015 | Choi |
| 2015/0245875 A1 | 9/2015 | Meenink |
| 2016/0278871 A1 | 9/2016 | Schena et al. |
| 2020/0146763 A1 | 5/2020 | Schena et al. |

FOREIGN PATENT DOCUMENTS

| | | |
|---|---|---|
| CN | 102176867 A | 9/2011 |
| JP | H07136173 A | 5/1995 |
| JP | H08509886 A | 10/1996 |
| JP | 2002103255 A | 4/2002 |
| JP | 2002530209 A | 9/2002 |
| JP | 2003299674 A | 10/2003 |
| JP | 2009106738 A | 5/2009 |
| JP | 2009540999 A | 11/2009 |
| KR | 20090089928 A | 8/2009 |
| KR | 20120014758 A | 2/2012 |
| WO | WO-9507055 A1 | 3/1995 |
| WO | WO-9950721 A1 | 10/1999 |
| WO | WO-2006039092 A2 | 4/2006 |
| WO | WO-2010040215 A1 | 4/2010 |
| WO | WO-2011060046 A2 | 5/2011 |
| WO | WO-2011149187 A2 | 12/2011 |

OTHER PUBLICATIONS

International Search Report and Written Opinion for Application No. PCT/US2013/043594, dated Sep. 5, 2013, 12 pages.
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

* cited by examiner

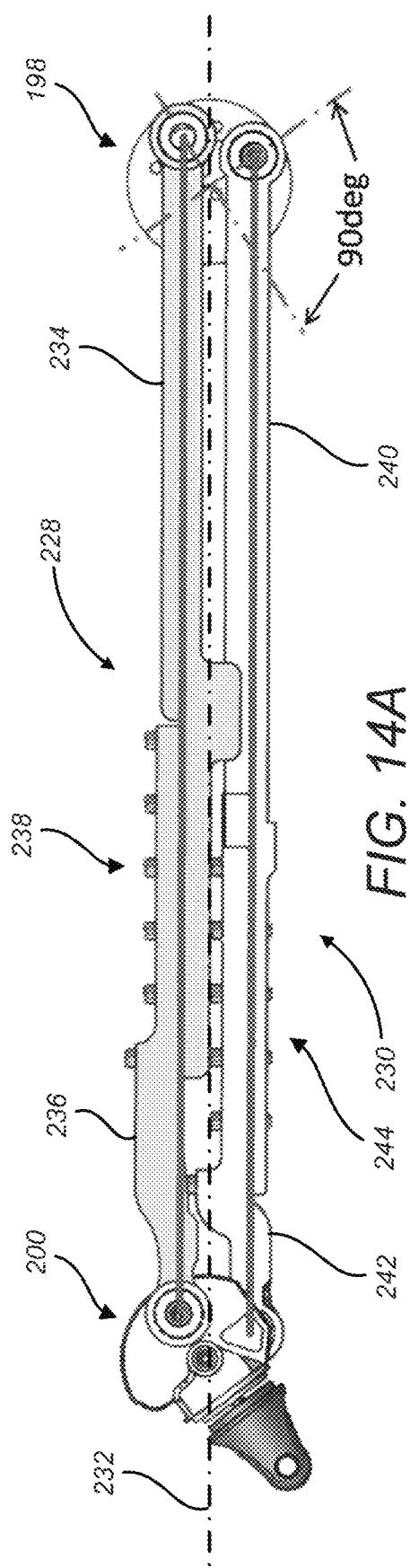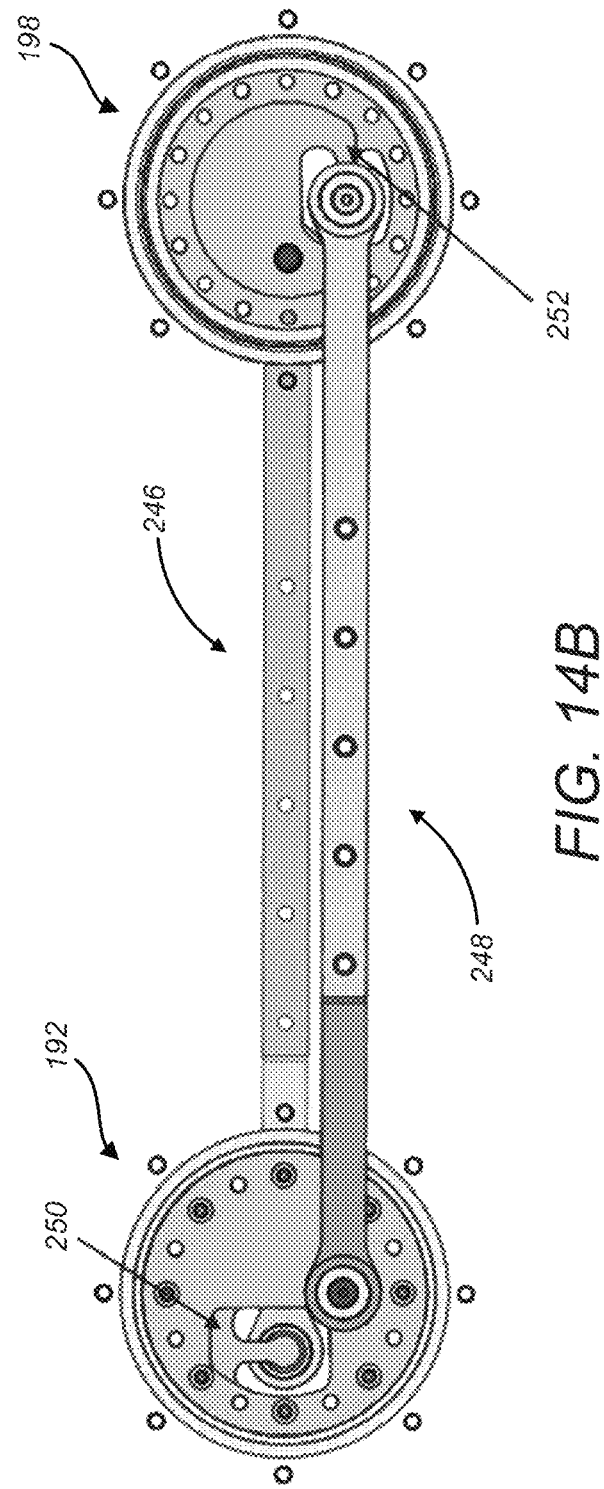
FIG. 14A
FIG. 14B

REDUNDANT AXIS AND DEGREE OF FREEDOM FOR HARDWARE-CONSTRAINED REMOTE CENTER ROBOTIC MANIPULATOR

CROSS-REFERENCE TO RELATED APPLICATION

The present application is a Continuation of U.S. application Ser. No. 15/058,914 filed Mar. 2, 2016 (Allowed), which is a Continuation of U.S. application Ser. No. 13/906,888 filed May 31, 2013, now U.S. Pat. No. 9,295,524 issued Mar. 29, 2016, which claims the benefit of U.S. Provisional Application No. 61/654,414 filed Jun. 1, 2012, the full disclosures of which are incorporated herein by reference in their entirety for all purposes.

BACKGROUND

Minimally invasive medical techniques are intended to reduce the amount of extraneous tissue that is damaged during diagnostic or surgical procedures, thereby reducing patient recovery time, discomfort, and deleterious side effects. One effect of minimally invasive surgery, for example, is reduced post-operative hospital recovery times. Because the average hospital stay for a standard open surgery is typically significantly longer than the average stay for an analogous minimally invasive surgery, increased use of minimally invasive techniques could save millions of dollars in hospital costs each year. While many of the surgeries performed each year in the United States could potentially be performed in a minimally invasive manner, only a portion of the current surgeries use these advantageous techniques due to limitations in minimally invasive surgical instruments and the additional surgical training involved in mastering them.

Minimally invasive robotic surgical or telesurgical systems have been developed to increase a surgeon's dexterity and avoid some of the limitations on traditional minimally invasive techniques. In telesurgery, the surgeon uses some form of remote control (e.g., a servomechanism, or the like) to manipulate surgical instrument movements, rather than directly holding and moving the instruments by hand. In telesurgery systems, the surgeon can be provided with an image of the surgical site at a surgical workstation. While viewing a two- or three-dimensional image of the surgical site on a display, the surgeon performs the surgical procedures on the patient by manipulating master control devices, which in turn control motion of the servo-mechanically operated slave instruments.

The servomechanism used for telesurgery will often accept input from two master controllers (one for each of the surgeon's hands) and may include two or more robotic arms on each of which a surgical instrument is mounted. Operative communication between master controllers and associated robotic arm and instrument assemblies is typically achieved through a control system. The control system typically includes at least one processor that relays input commands from the master controllers to the associated robotic arm and instrument assemblies and back from the instrument and arm assemblies to the associated master controllers in the case of, for example, force feedback or the like. One example of a robotic surgical system is the DA VINCI® system commercialized by Intuitive Surgical, Inc. of Sunnyvale, Calif.

A variety of structural arrangements have been used to support the surgical instrument at the surgical site during robotic surgery. The driven linkage or "slave" is often called a robotic surgical manipulator, and exemplary linkage arrangements for use as a robotic surgical manipulator during minimally invasive robotic surgery are described in U.S. Pat. No. 7,594,912 (filed Sep. 30, 2004), U.S. Pat. No. 6,758,843 (filed Apr. 26, 2002), U.S. Pat. No. 6,246,200 (filed Aug. 3, 1999), and U.S. Pat. No. 5,800,423 (filed Jul. 20, 1995), the full disclosures of which are incorporated herein by reference. These linkages often manipulate an instrument holder to which an instrument having a shaft is mounted. Such a manipulator structure can include a parallelogram linkage portion that generates motion of the instrument holder that is limited to rotation about a pitch axis that intersects a remote center of manipulation located along the length of the instrument shaft. Such a manipulator structure can also include a yaw joint that generates motion of the instrument holder that is limited to rotation about a yaw axis that is perpendicular to the pitch axis and that also intersects the remote center of manipulation. By aligning the remote center of manipulation with the incision point to the internal surgical site (for example, with a trocar or cannula at an abdominal wall during laparoscopic surgery), an end effector of the surgical instrument can be positioned safely by moving the proximal end of the shaft using the manipulator linkage without imposing potentially hazardous forces against the abdominal wall. Alternative manipulator structures are described, for example, in U.S. Pat. No. 6,702,805 (filed Nov. 9, 2000), U.S. Pat. No. 6,676,669 (filed Jan. 16, 2002), U.S. Pat. No. 5,855,583 (filed Nov. 22, 1996), U.S. Pat. No. 5,808,665 (filed Sep. 9, 1996), U.S. Pat. No. 5,445,166 (filed Apr. 6, 1994), and U.S. Pat. No. 5,184,601 (filed Aug. 5, 1991), the full disclosures of which are incorporated herein by reference.

While the new telesurgical systems and device have proven highly effective and advantageous, still further improvements would be desirable. In general, it would be desirable to provide improved structures and systems for performing minimally invasive robotic surgery. More specifically, it would be beneficial to enhance the efficiency and ease of use of these systems. For example, it would be particularly beneficial to improve the range of motion provided by the robotic surgical manipulator without imposing potentially hazardous forces against the abdominal wall.

BRIEF SUMMARY

The following presents a simplified summary of some embodiments of the invention in order to provide a basic understanding of the invention. This summary is not an extensive overview of the invention. It is not intended to identify key/critical elements of the invention or to delineate the scope of the invention. Its sole purpose is to present some embodiments of the invention in a simplified form as a prelude to the more detailed description that is presented later.

Improved remote center manipulators are disclosed that support a surgical instrument and provide a center of manipulation, remote from any bearings or mechanical supports, at a desired location of the instrument during minimally invasive robotic surgery. The remote center manipulator constrains the instrument to move around the remote center of manipulation, which is preferably coincident with an entry incision in a patient, such as the patient's abdominal wall. In many embodiments, the manipulator linkage includes (1) rotationally coupled joints that generate parallelogram motion used to pitch the surgical instrument around a first axis passing through the remote center of manipulation, (2) rotationally coupled links to generate motion that is used to roll the surgical instrument around a second axis passing through the remote center of manipulation, and (3) at least one additional pair of links coupled to rotate about an associated additional axis that passes through the remote center of manipulation. In addition to passing through the remote center of manipulation, the associated additional axis is not coincident with either of the first axis or the second axis, thereby allowing the rotation around the one or more additional axes to be used to improve the range of motion provided by the robotic surgical manipulator without imposing potentially hazardous forces against the abdominal wall.

Thus, in one aspect, a remote center manipulator is disclosed for constraining a position of a surgical instrument during minimally invasive robotic surgery. The surgical instrument includes an elongate shaft. The shaft has a distal working end configuration configured for insertion along an insertion axis into a body cavity of a patient through a remote center of manipulation. The remote center manipulator includes a base link configured to be held in a fixed position relative to the patient, an instrument holder configured to couple with the surgical instrument; and a linkage coupling the instrument holder to the base link. First and second links of the linkage are coupled to limit motion of the second link relative to the first link to rotation about a first axis intersecting the remote center of manipulation. The linkage further includes three rotationally coupled rotary joints configured to generate constrained parallelogram motion of the linkage by which motion of the instrument holder is limited to rotation about a second axis intersecting the remote center of manipulation. The second axis is not coincident to the first axis. Third and fourth links of the linkage are coupled to limit motion of the fourth link relative to the third link to rotation about a third axis intersecting the remote center of manipulation. The third axis is not coincident to either of the first and second axes.

In many embodiments, the coupling between the third and fourth links is disposed between the base link and the coupling between the first and second links. In such embodiments, the motion of the fourth link serves to reposition the majority of the linkage without moving the remote center of manipulation relative to the patient. For example, the third link can be the base link or at least fixed relative to the base link. The fourth link can be the first link or at least fixed relative to the first link. In many embodiments, the angle between the first axis and the third axis is between 10 degrees and 30 degrees. For example, the angle between the first axis and the third axis is approximately 15 degrees. In many embodiments, the first axis and the third axis are perpendicular or substantially (i.e., within acceptable tolerance) perpendicular.

In many embodiments, the first axis and the second axis are perpendicular or substantially perpendicular. Such a configuration provides for well-conditioned control over the movement of the instrument holder.

In many embodiments, the linkage includes an intermediate conical sweep joint. For example, in many embodiments, the links of the linkage form a serially connected assembly of links. The third link can be located between the second link and the instrument holder in the serially connected assembly of links. And the fourth link can be at least one of fixed relative to the instrument holder or be the instrument holder. In many embodiments, the linkage is operable to orient the fourth link relative to the third link so that the surgical instrument elongate shaft lies in a plane defined by the first axis and the third axis.

In many embodiments, the remote center manipulator includes Sine/Cosine links that drivingly couple at least one pair of the three rotationally coupled rotary joints that are configured to generate the constrained parallelogram motion of the linkage. And in many embodiments, the Sine/Cosine links with oriented flexures drivingly couple at least one pair of the three rotationally coupled rotary joints that are configured to generate the constrained parallelogram motion of the linkage.

In another aspect, a remote center manipulator is disclosed for constraining a position of a surgical instrument during minimally invasive robotic surgery. The surgical instrument includes an elongated shaft. The shaft has a distal working end configured for insertion into a body cavity of a patient through a remote center of manipulation. The remote center manipulator includes a mounting base, a conical sweep link, and first through fourth links. The conical sweep link has a conical sweep link proximal end and a conical sweep link distal end. The conical sweep link proximal end is coupled to the mounting base for rotation about a first axis that intersects the remote center of manipulation. The first link has a first link proximal end and a first link distal end. The first link proximal end is coupled with the conical sweep link distal end for rotation about a second axis that intersects the remote center of manipulation. The second axis is not coincident to the first axis. The second link has a second link proximal end and a second link distal end. The second link proximal end is rotationally coupled to the first link distal end at a first parallelogram linkage joint. The third link has a third link proximal end and a third link distal end. The third link proximal end is rotationally coupled to the second link distal end at a second parallelogram linkage joint. The fourth link is configured to support the surgical instrument. The fourth link is rotationally coupled to the third link distal end by a third parallelogram linkage joint. The first, second, and third parallelogram linkage joints are rotationally coupled such that rotation of the first parallelogram joint generates motion of the fourth link that is limited to rotation about a third axis that intersects the remote center of manipulation. The third axis is not coincident with either of the first axis or the third axis.

In many embodiments, the angle between the first axis and the second axis is between 10 degrees and 30 degrees. For example, the angle between the first axis and the second axis can be approximately 15 degrees.

In many embodiments, the conical sweep link is configured to be stiff relative to torsion and bending loading without excessive weight. For example, in many embodiments the conical sweep link has a conical sweep link body section connecting the conical sweep link first end to the conical sweep link second end. In many embodiments, the conical sweep link body section has a box cross-sectional configuration or a tube-like configuration.

In many embodiments, the manipulator further includes a conical sweep joint rotationally coupling the fourth link to the third link distal end for rotation about a fourth axis that intersects the remote center of manipulation. The fourth axis is not coincident with any of the first axis, the second axis, or the third axis. In many embodiments, the conical sweep joint is operable to orient the fourth link relative to the third link so that the surgical instrument elongate shaft lies in a plane defined by the second axis and the fourth axis.

In many embodiments, the manipulator includes Sine/Cosine links that drivingly couple at least one pair of the first, second, and third parallelogram linkage joints. And in many embodiments, the Sine/Cosine links with oriented flexures drivingly couple at least one pair of the first, second, and third parallelogram linkage joints.

In another aspect, a remote center manipulator is disclosed for constraining a position of a surgical instrument during minimally invasive robotic surgery. The surgical instrument includes an elongated shaft. The shaft has a distal working end configured for insertion into a body cavity of a patient through a remote center of manipulation. The remote center manipulator includes a mounting base, and first through fifth links. The first link is coupled with the mounting base so as to be selectively repositionable relative to the mounting base. Movement of the first link relative to the second link is limited to rotation about a first axis that intersects the remote center of manipulation. The second link has a second link proximal end and a second link distal end. The second link proximal end is coupled to the first link for rotation about a second axis that intersects the remote center of manipulation. The second axis is not coincident to the first axis. The third link has a third link proximal end and a third link distal end. The third link proximal end is rotationally coupled to the second link distal end at a first parallelogram linkage joint. The fourth link has a fourth link proximal end and a fourth link distal end. The fourth link proximal end is rotationally coupled to the second link distal end at a second parallelogram linkage joint. The fifth link is configured to support the surgical instrument. The fifth link is rotationally coupled to the fourth link distal end at a third parallelogram linkage joint. The first, second, and third parallelogram linkage joints are rotationally coupled such that rotation of the first parallelogram joint generates motion of the fifth link that is limited to rotation about a third axis that intersects the remote center of manipulation. The third axis is not coincident with either of the first axis or the second axis.

In many embodiments, the mounting base includes a curved feature to which the first link is interfaced such that the first link is constrained to move along the curved feature. The curved feature has a constant radius of curvature relative to the remote center of manipulation.

In many embodiments, the mounting base includes a closed-loop curved feature to which the first link is interfaced. The first link is constrained to move along the closed-loop curved feature.

In many embodiments, the manipulator includes Sine/Cosine links that drivingly couple at least one pair of the first, second, and third parallelogram linkage joints. And in many embodiments, the Sine/Cosine links with oriented flexures drivingly couple at least one pair of the first, second, and third parallelogram linkage joints.

For a fuller understanding of the nature and advantages of the present invention, reference should be made to the ensuing detailed description and accompanying drawings. Other aspects, objects and advantages of the invention will be apparent from the drawings and detailed description that follows.

BRIEF DESCRIPTION OF THE DRAWINGS

FIG. 14A illustrates Sine/Cosine links that can be used to rotationally couple two parallelogram joints in the remote center manipulator of FIG. 8, in accordance with many embodiments.

FIG. 14B illustrates oriented flexures that serve to alleviate force-fight induced loads in links used to rotationally couple two parallelogram joints in a remote center manipulator, in accordance with many embodiments.

DETAILED DESCRIPTION

In the following description, various embodiments of the present invention will be described. For purposes of explanation, specific configurations and details are set forth in order to provide a thorough understanding of the embodiments. However, it will also be apparent to one skilled in the art that the present invention may be practiced without the specific details. Furthermore, well-known features may be omitted or simplified in order not to obscure the embodiment being described.

Minimally Invasive Robotic Surgery

Figure 1:
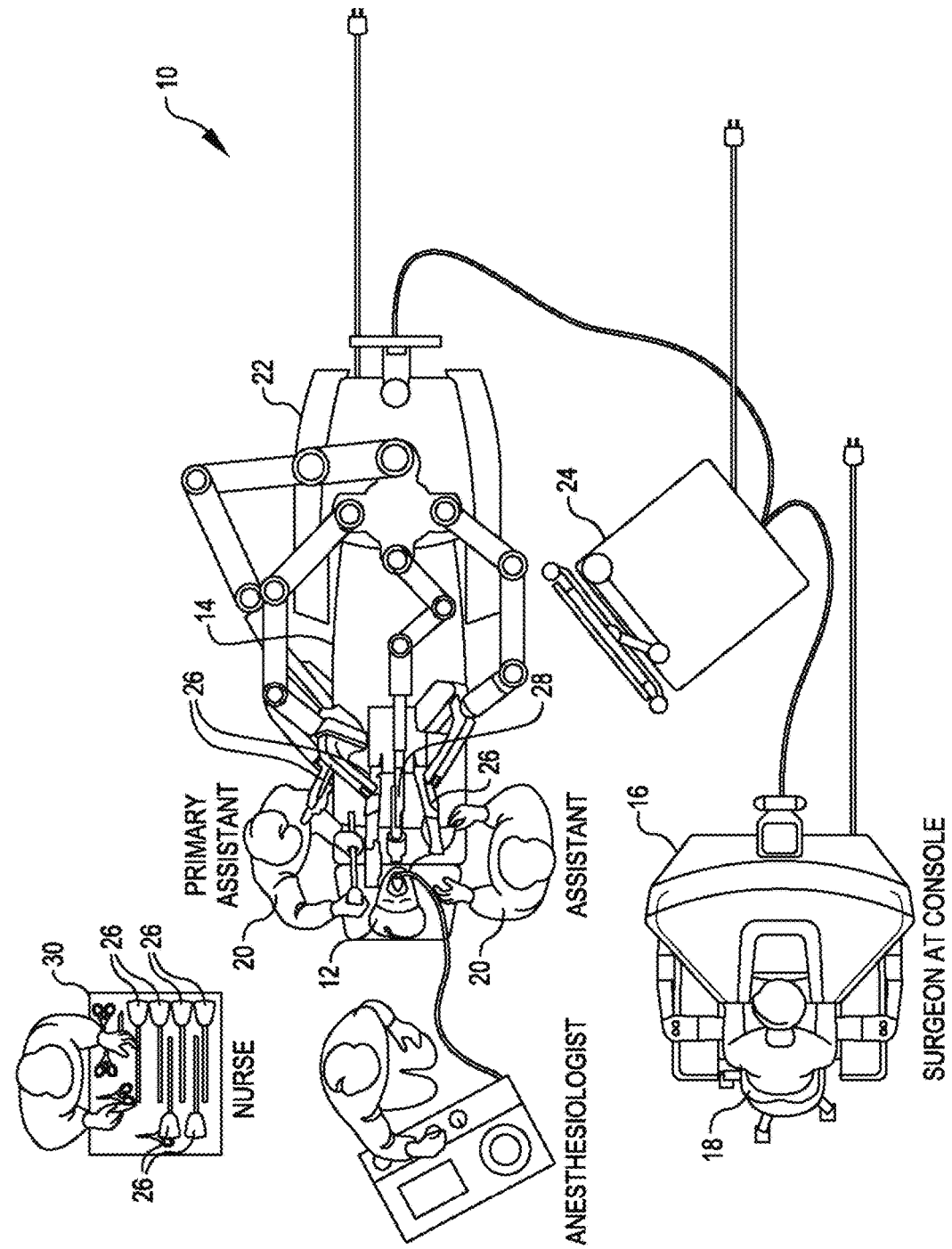
FIG. 1 is a plan view of a minimally invasive robotic surgery system being used to perform a surgery, in accordance with many embodiments.

Referring now to the drawings, in which like reference numerals represent like parts throughout the several views, FIG. 1 is a plan view illustration of a Minimally Invasive Robotic Surgical (MIRS) system 10, typically used for performing a minimally invasive diagnostic or surgical procedure on a Patient 12 who is lying on an Operating table 14. The system can include a Surgeon's Console 16 for use by a Surgeon 18 during the procedure. One or more Assistants 20 may also participate in the procedure. The MIRS system 10 can further include a Patient Side Cart 22 (surgical robot) and an Electronics Cart 24. The Patient Side Cart 22 can manipulate at least one removably coupled tool assembly 26 (hereinafter referred to as a "tool") through a minimally invasive incision in the body of the Patient 12 while the Surgeon 18 views an image of the surgical site through the Console 16. An image of the surgical site can be obtained by an endoscope 28, such as a stereoscopic endoscope, which can be manipulated by the Patient Side Cart 22 to position and orient the endoscope 28. The Electronics Cart 24 can be used to process the images of the surgical site for subsequent display to the Surgeon 18 through the Surgeon's Console 16. The number of surgical tools 26 used at one time will generally depend on the diagnostic or surgical procedure and the space constraints within the operating room, among other factors. If it is necessary to change one or more of the tools 26 being used during a procedure, an Assistant 20 may remove the tool 26 from the Patient Side Cart 22 and replace it with another tool 26 from a tray 30 in the operating room.

Figure 2:
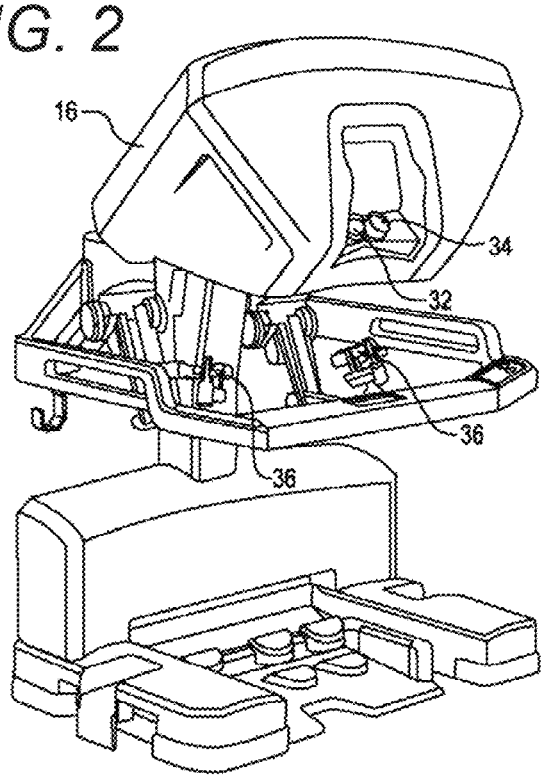
FIG. 2 is a perspective view of a surgeon's control console for a robotic surgery system, in accordance with many embodiments.

FIG. 2 is a perspective view of the Surgeon's Console 16. The Surgeon's Console 16 includes a left eye display 32 and a right eye display 34 for presenting the Surgeon 18 with a coordinated stereo view of the surgical site that enables depth perception. The Console 16 further includes one or more input control devices 36, which in turn cause the Patient Side Cart 22 (shown in FIG. 1) to manipulate one or more tools. The input control devices 36 can provide the same degrees of freedom as their associated tools 26 (shown in FIG. 1) to provide the Surgeon with telepresence, or the perception that the input control devices 36 are integral with the tools 26 so that the Surgeon has a strong sense of directly controlling the tools 26. To this end, position, force, and tactile feedback sensors (not shown) may be employed to transmit position, force, and tactile sensations from the tools 26 back to the Surgeon's hands through the input control devices 36. Each individual input control device 36 acts as a human-controlled master to control a corresponding slave surgical tool to enable teleoperation. The telepresence sensation is enabled when this teleoperation is combined with the display of the surgical site perceived in three dimensions and the surgeon's hand positioned on a master at a position corresponding with the viewed tool image at the surgical site.

The Surgeon's Console 16 is usually located in the same room as the patient so that the Surgeon may directly monitor the procedure, be physically present if necessary, and speak to an Assistant directly rather than over the telephone or other communication medium. However, the Surgeon can be located in a different room, a completely different building, or other remote location from the Patient allowing for remote surgical procedures.

Figure 3:
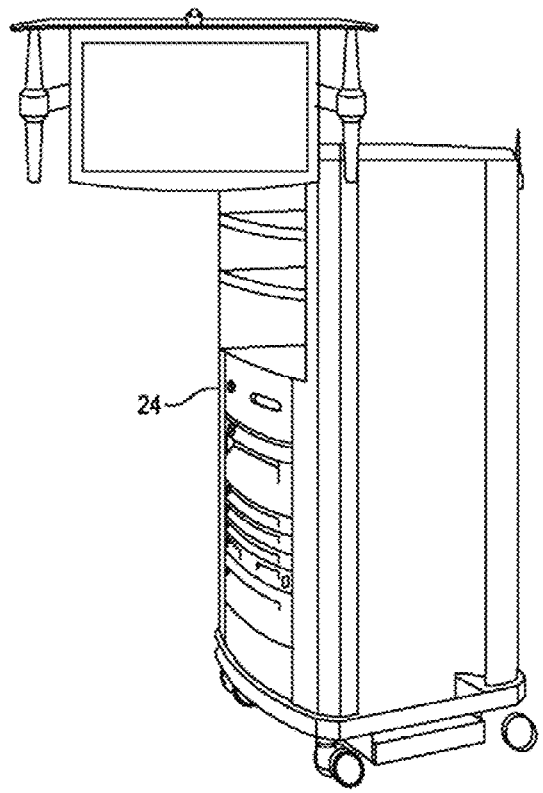
FIG. 3 is a perspective view of a robotic surgery system electronics cart, in accordance with many embodiments.

FIG. 3 is a perspective view of the Electronics Cart 24. The Electronics Cart 24 can be coupled with the endoscope 28 and can include a processor to process captured images for subsequent display, such as to a Surgeon on the Surgeon's Console, or on another suitable display located locally and/or remotely. For example, where a stereoscopic endoscope is used, the Electronics Cart 24 can process the captured images to present the Surgeon with coordinated stereo images of the surgical site. Such coordination can include alignment between the opposing images and can include adjusting the stereo working distance of the stereoscopic endoscope. As another example, image processing can include the use of previously determined camera calibration parameters to compensate for imaging errors of the image capture device, such as optical aberrations.

Figure 4:
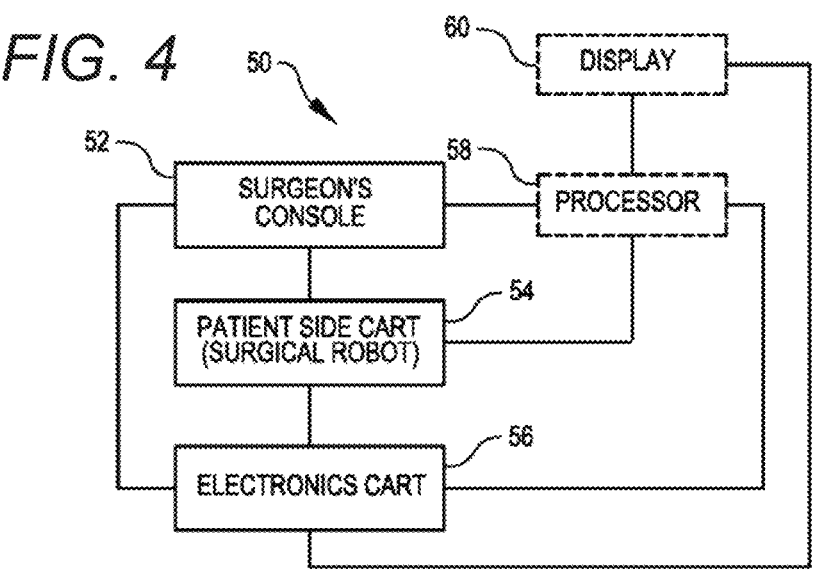
FIG. 4 diagrammatically illustrates a robotic surgery system, in accordance with many embodiments.

FIG. 4 diagrammatically illustrates a robotic surgery system 50 (such as MIRS system 10 of FIG. 1). As discussed above, a Surgeon's Console 52 (such as Surgeon's Console 16 in FIG. 1) can be used by a Surgeon to control a Patient Side Cart (Surgical Robot) 54 (such as Patent Side Cart 22 in FIG. 1) during a minimally invasive procedure. The Patient Side Cart 54 can use an imaging device, such as a stereoscopic endoscope, to capture images of the procedure site and output the captured images to an Electronics Cart 56 (such as the Electronics Cart 24 in FIG. 1). As discussed above, the Electronics Cart 56 can process the captured images in a variety of ways prior to any subsequent display. For example, the Electronics Cart 56 can overlay the captured images with a virtual control interface prior to displaying the combined images to the Surgeon via the Surgeon's Console 52. The Patient Side Cart 54 can output the captured images for processing outside the Electronics Cart 56. For example, the Patient Side Cart 54 can output the captured images to a processor 58, which can be used to process the captured images. The images can also be processed by a combination the Electronics Cart 56 and the processor 58, which can be coupled together to process the captured images jointly, sequentially, and/or combinations thereof. One or more separate displays 60 can also be coupled with the processor 58 and/or the Electronics Cart 56 for local and/or remote display of images, such as images of the procedure site, or other related images.

Figure 5A:
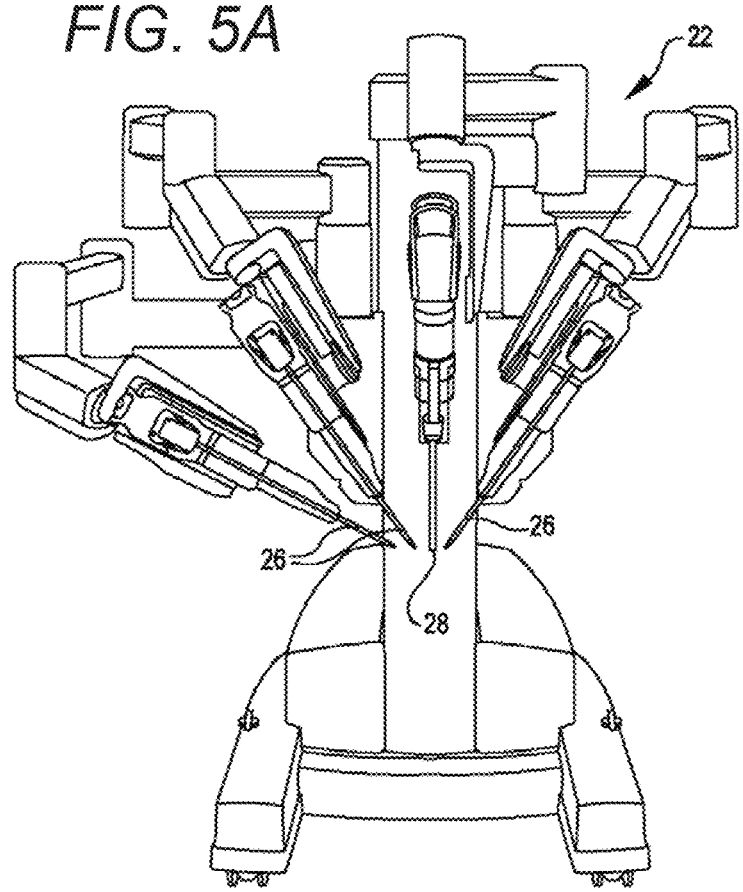
FIG. 5A is a front view of a patient side cart (surgical robot) of a robotic surgery system, in accordance with many embodiments.
Figure 5B:
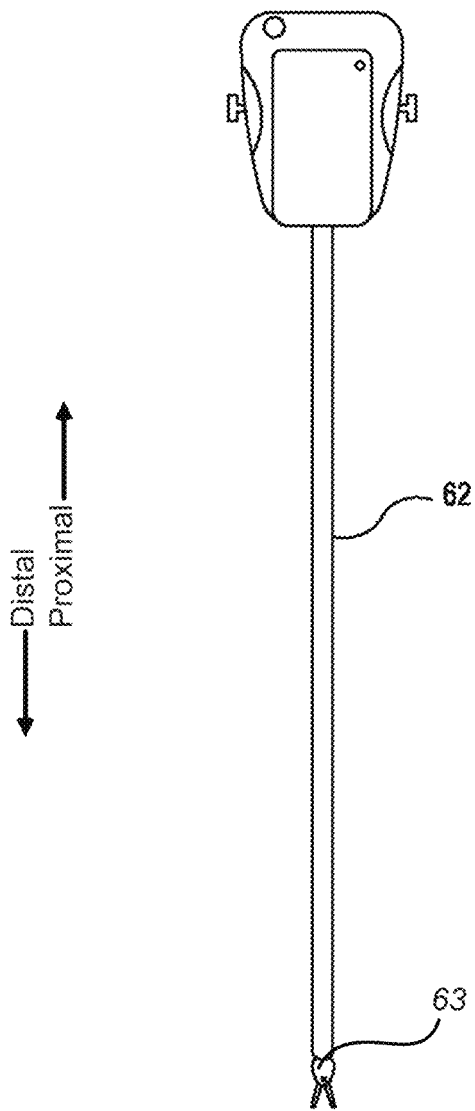
FIG. 5B is a front view of a robotic surgery tool, in accordance with many embodiments.

FIGS. 5A and 5B show a Patient Side Cart 22 and a surgical tool 62, respectively. The surgical tool 62 is an example of the surgical tools 26. The Patient Side Cart 22 shown provides for the manipulation of three surgical tools 26 and an imaging device 28, such as a stereoscopic endoscope used for the capture of images of the site of the procedure. Manipulation is provided by robotic mechanisms having a number of robotic joints. The imaging device 28 and the surgical tools 26 can be positioned and manipulated through incisions in the patient so that a kinematic remote center of motion is maintained at the incision to minimize the size of the incision. Images of the surgical site can include images of the distal ends of the surgical tools 26 when they are positioned within the field-of-view of the imaging device 28. A diagnostic or therapeutic end effector 63 is typically at the distal end of the surgical instrument's long shaft.

Hardware-Constrained Remote Center Manipulators

Figure 6:
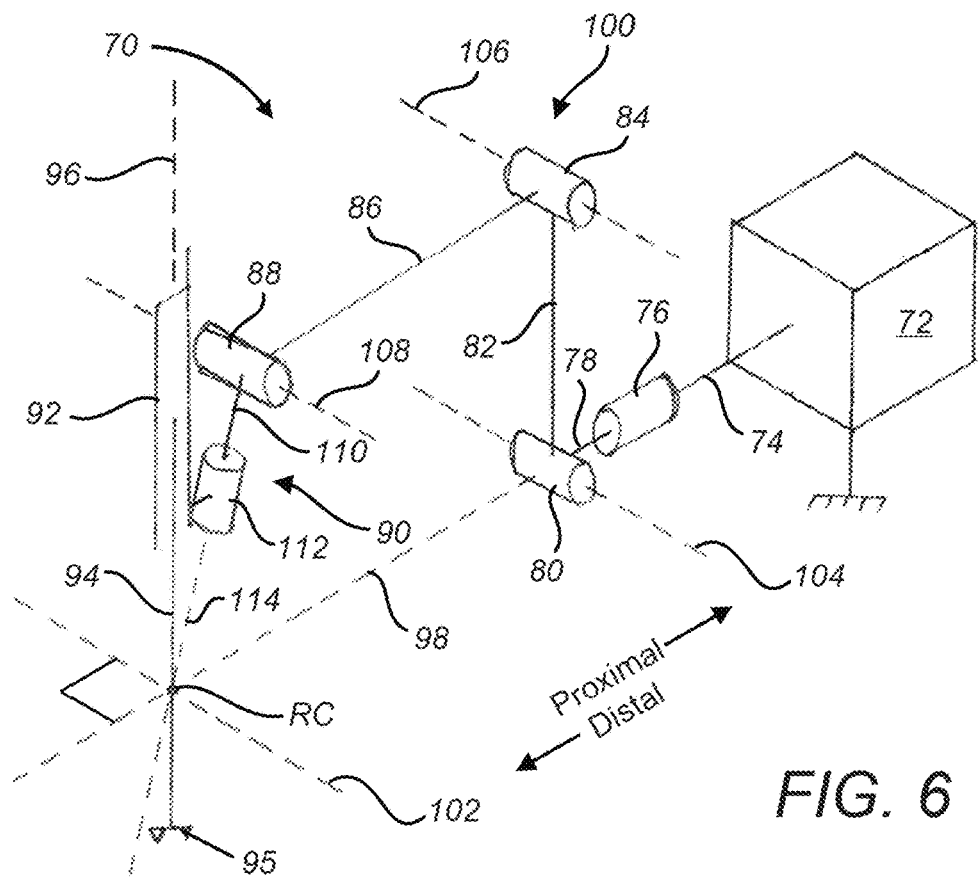
FIG. 6 is a perspective schematic representation of a remote center manipulator, in accordance with many embodiments, that includes a conical sweep joint operable to reorient an instrument holder without moving a remote center of manipulation.

FIG. 6 is a perspective schematic representation of a remote center manipulator 70, in accordance with many embodiments. The remote center manipulator 70 is supported from a mounting base 72. The remote center manipulator 70 includes a base link 74 that is supported by the mounting base 72, a yaw joint 76, an extension link 78, a base parallelogram joint 80, a first parallelogram link 82, a first parallelogram joint 84, a second parallelogram link 86, a second parallelogram joint 88, a conical sweep mechanism 90, and an instrument holder 92. The instrument holder 92 is configured to support and translate a surgical instrument 94 along an insertion axis 96 (i.e., instrument holder 92 includes at least one prismatic joint that moves surgical instrument 94 in and out of the incision at the patient's body wall or at the patient's natural body orifice along insertion axis 96). A surgical end effector 95 is at the distal end of surgical instrument 94. The end effector may be for any surgical function, including therapeutic, diagnostic, or imaging surgical devices. End effector roll may be done in various known ways. For example, instrument holder 92 or instrument 94 itself may include an instrument shaft roll capability that allows the instrument shaft to roll around insertion axis 96. As an alternative example, the shaft may remain stationary in roll, and the end effector rolls at the end of the instrument shaft.

The mounting base 72 allows the remote center manipulator 70 to be mounted and supported by set-up arms/joints of a cart mount, a ceiling mount, floor/pedestal mount, or other mounting surface so that the base remains effectively stationary in a ground reference frame (as represented by the ground symbol). The remote center manipulator 70 is configured such that the remote center of manipulation (RC) does not move relative to the mounting base 72 as the surgical instrument 94 is manipulated. By supporting the mounting base 72 in a fixed position and orientation relative to a patient, a remote center of manipulation (RC) is held fixed relative to the patient, thereby providing an entry point for the surgical instrument 94. With the remote center of manipulation (RC) fixed relative to the patient, the manipulation of the surgical instrument 94 can be accomplished without the risk of imposing potentially hazardous forces on patient tissue at the entry location of the surgical instrument 94. In embodiments in which the surgical instrument shaft passes through a cannula, the remote center of manipulation is typically defined at a point along the cannula's centerline, although in some embodiments a cannula may be optional.

The yaw joint 76 rotationally couples the proximal end of the extension link 78 to the distal end of the base link 74. The yaw joint 76 is operable to produce controlled rotation (roll) of the extension link 78 about a yaw axis 98 that extends through the remote center of manipulation (RC). Because the instrument holder 92 is coupled to the extension link 78 via the intervening linkage components of the remote center manipulator 70, rotation (roll) of the extension link 78 about the yaw axis 98 generates corresponding rotation of the instrument holder 92 about the yaw axis 98, thereby maintaining the position and orientation of the remote center of manipulation (RC) relative to the mounting base 72 for all angular orientations of the yaw joint 76. The term "yaw" is arbitrary, and under this term it can be seen that with the remote center of manipulation (RC) stationary, rotation around yaw axis 98 will cause the distal tip of surgical instrument 94 to move in a way defined as yaw.

A parallelogram linkage portion 100 of the remote center manipulator 70 is configured to produce motion of the instrument holder 92 that is limited to rotation about a pitch axis 102 that intersects the remote center of manipulation (RC). By limiting the corresponding movement of the instrument holder 92 to rotation (pitch) about the pitch axis 102, the insertion axis 96 continually intersects the remote center of manipulation (RC) and the distance between the instrument holder 92 and the remote center of manipulation (RC) is maintained. The term "pitch" is arbitrary, and under this term it can be seen that with the remote center of manipulation (RC) stationary, rotation around pitch axis 102 will cause the distal tip of surgical instrument 94 to move in a way defined as pitch.

The parallelogram linkage portion 100 includes the parallelogram base joint 80, the first parallelogram link 82, the first parallelogram joint 84, the second parallelogram link 86, the second parallelogram joint 88, the conical sweep mechanism 90, and the instrument holder 92. The base parallelogram joint 80 rotationally couples the proximal end of the first parallelogram link 82 to the distal end of the extension link 78. The base parallelogram joint 80 is operable to produce controlled rotation of the first parallelogram link 82 about a base joint axis 104 that is parallel to the pitch axis 102. The position and orientation of the base joint axis 104 is fixed relative to the extension link 78. The first parallelogram joint 84 rotationally couples the proximal end of the second parallelogram link 86 to the distal end of the first parallelogram link 82 for rotation of the second parallelogram link 86 about a first joint axis 106 that is parallel to the pitch axis 102. The position and orientation of the first joint axis 106 is fixed relative to the first parallelogram link 82. The second parallelogram joint 88 rotationally couples the proximal end of the conical sweep mechanism 90 to the distal end of the second parallelogram link 86 for rotation of the conical sweep mechanism 90 about a second joint axis 108 that is parallel to the pitch axis 102. The position and orientation of the second joint axis 108 is fixed relative to the second parallelogram link 86. Because the instrument holder 92 is coupled to the distal end of the conical sweep mechanism 90, the instrument holder 92 is constrained to rotate about the second joint axis 108.

The first and second parallelogram joints 84, 88 are rotationally coupled to the base parallelogram joint 80 so that actuation of the base parallelogram joint 80 actuates the parallelogram linkage portion 100, thereby generating corresponding motion of the instrument holder 92 that is limited to rotation about the pitch axis 102. Any suitable approach can be used to rotationally couple the base parallelogram joint 80, the first parallelogram joint 84, and the second parallelogram joint 88. For example, the base parallelogram joint 80 can include a base pulley that is rotationally fixed to the extension link 78 and mounted to rotate relative to the first parallelogram link 82 around the base joint axis 104. The first parallelogram joint 84 can include a first pulley that is rotationally fixed to the second parallelogram link 86 and mounted to rotate relative to the first parallelogram link 82 around the first joint axis 106. By tying the rotation of the first pulley to rotation of the second pulley, for example by one or more drive belts or one or more links, rotation of the second parallelogram link 86 relative to the first parallelogram link 82 can be driven by rotation of the first parallelogram link 82 relative to the extension link 78 such that the same relative orientation between the second parallelogram link 86 and the extension link 78 is maintained for all angular orientation of the first parallelogram link 82 relative to the extension link 78. In a like manner, the first parallelogram joint 84 can include a third pulley that is rotationally fixed to the first parallelogram link 82 and mounted to rotate relative to the second parallelogram link 86 around the first joint axis 106. The second parallelogram joint 88 can include a fourth pulley that is rotationally fixed to the proximal end of the conical sweep mechanism 90 and mounted to rotate relative to the second parallelogram link 86 around the second joint axis 108. By tying the rotation of the third pulley to rotation of the fourth pulley, for example by one or more drive belts or one or more links, rotation of the conical sweep mechanism 90 relative to the second parallelogram link 86 can be driven by rotation of the second parallelogram link 86 relative to the first parallelogram link 82 such that the same relative orientation between the insertion axis 96 and the first parallelogram link 82 is maintained for all angular orientation of the second parallelogram link 86 relative to the first parallelogram link 82.

The conical sweep mechanism 90 includes a proximal conical sweep link 110 and a conical sweep joint 112. The conical sweep joint 112 rotationally couples the instrument holder 92 to the proximal conical sweep link 110 such that actuation of the conical sweep joint 112 reorients the instrument holder 92 relative to the proximal conical sweep link 110 about a conical sweep axis 114 that intersects the remote center of manipulation (RC). Rotation of conical sweep joint 112 causes the shaft of surgical instrument 94 to sweep along the surface of a cone centered on conical sweep axis 114 and having a vertex at the remote center of manipulation (RC). Reorientation of the instrument holder 92 about the conical sweep axis 114 can be used for any suitable purpose, such as for collision avoidance with an adjacent surgical manipulator and/or the patient, or for providing increased space at the body wall to allow surgical personnel to access the sterile surgical field where the instrument enters the body. Reorientation of the instrument holder 92 about the conical sweep axis 114 can also be used to extend the available movement range of the instrument holder 92 relative to the patient. The conical sweep axis 114 provides one redundant axis about which the instrument holder 92 can be rotated around the remote center of manipulation (RC). The conical sweep axis 114 is not aligned with any of the yaw axis 98, the pitch axis 102, or the insertion axis 96. In operation, however, the angle between the conical sweep axis 114 and the yaw axis 98 can change as the remote center manipulator 70 is articulated. Conical sweep mechanism 90 is optional and may be included or not with various manipulator embodiments as described herein. For purposes of this description, conical sweep mechanism 90 may be considered a distal conical sweep mechanism to distinguish it from other conical sweep mechanisms located more proximally in the manipulator (see e.g., FIG. 8 in which another, "proximal" conical sweep mechanism is shown).

Figure 7:
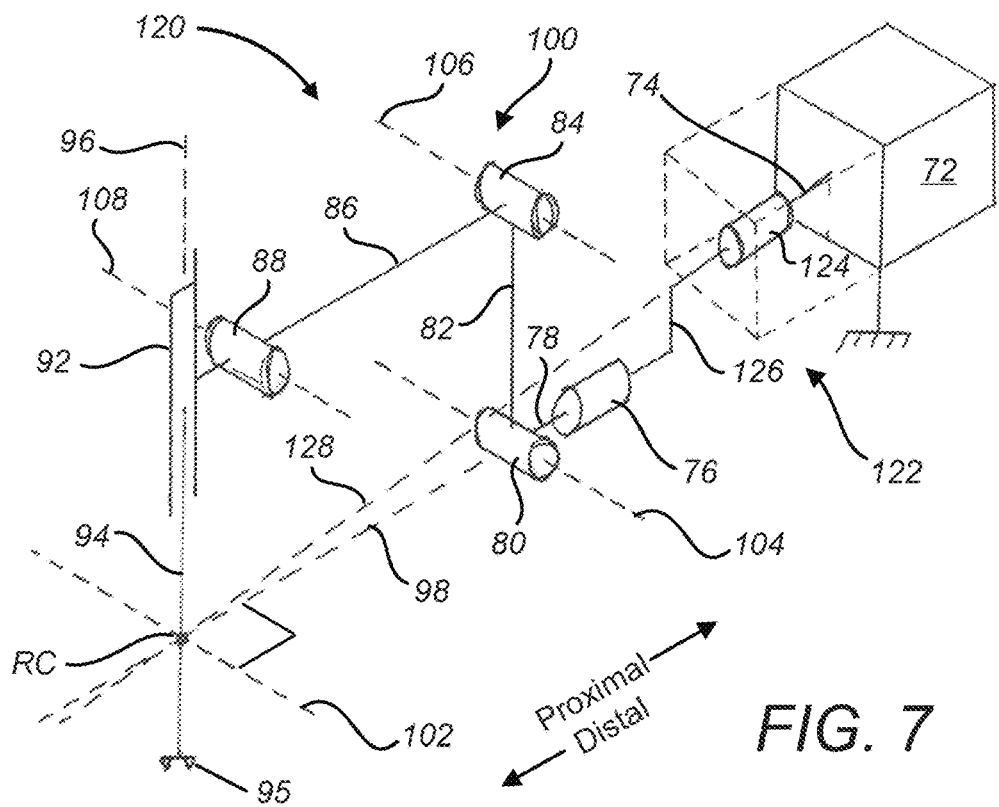
FIG. 7 is a perspective schematic representation of a remote center manipulator, in accordance with many embodiments, that includes a conical sweep link operable to reorient the outboard portion of the manipulator without moving a remote center of manipulation.

FIG. 7 is a perspective schematic representation of a remote center manipulator 120, in accordance with many embodiments. The remote center manipulator 120 includes some of the same components as the remote center manipulator 70 of FIG. 6. The shared components include the mounting base 72, the base link 74, the yaw joint 76, the extension link 78, the base parallelogram joint 80, the first parallelogram link 82, the first parallelogram joint 84, the second parallelogram link 86, the second parallelogram joint 88, and the instrument holder 92. The remote center manipulator 120 does not include the conical sweep mechanism 90. Instead, the second parallelogram joint 88 rotationally couples the instrument holder 92 to the second parallelogram link 86 for rotation of the instrument holder 92 relative to the second parallelogram link 86 about the second joint axis 108.

The remote center manipulator 120 further includes a conical sweep mechanism 122. The conical sweep mechanism 122 includes a conical sweep joint 124 and a conical sweep link 126 that is rotationally coupled to the base link 74 by the conical sweep joint 124. The conical sweep joint 124 is operable to selectively rotate the conical sweep link 126 around a conical sweep axis 128 that intersects the remote center of manipulation (RC). The distal end of the conical sweep link 126 supports the yaw joint 76. The conical sweep link 126 is configured to position and orient the yaw joint 76 such that the yaw axis 98 intersects the remote center of manipulation (RC) for all orientations of the conical sweep link 126 around the conical sweep axis 128. The conical sweep mechanism 122 is operable to reorient the outboard linkage of the remote center manipulator 120 relative to the mounting base 72 while maintaining the position of the remote center of manipulation (RC) relative to the mounting base 72. Rotation of conical sweep joint 124 causes the shaft of surgical instrument 94 to sweep along the surface of a cone centered on conical sweep axis 128 and having a vertex at the remote center of manipulation (RC). The conical sweep mechanism 122 can be used in any suitable fashion, for example, as a set-up joint that is used to position/orient the outboard portion of the remote center manipulator 120 prior to a surgical procedure and/or used to position/orient the outboard portion of the remote center manipulator 120 actively during a surgical procedure. The conical sweep axis 128 provides a redundant degree of freedom axis about which the instrument holder 92 can be rotated around the remote center of manipulation (RC). The conical sweep axis 128 is not aligned with any of the yaw axis 92, the pitch axis 102, or the insertion axis 96. The conical sweep axis 128 can be offset from the yaw axis 98 by any suitable angle (e.g., 15 degrees in one embodiment). Referring again to FIG. 6, conical sweep mechanism 122 is optional and may be included or not with various manipulator embodiments as described herein. For purposes of this description, conical sweep mechanism 122 may be considered a proximal conical sweep mechanism to distinguish it from other conical sweep mechanisms located more distally in the manipulator (see e.g., FIG. 8 in which another, "distal" conical sweep mechanism is shown).

The joint associated with conical sweep mechanism 122 may be powered or unpowered, and if powered can be under active surgeon control as part of the teleoperation function or passively controlled by another person in the operating room. If passively controlled by a person other than the surgeon, conical sweep mechanism can be used as part of the set-up structure to properly position the remote center manipulator for surgery before and/or during a surgical procedure. In some embodiments, a switch (pushbutton, rocker, etc.) controls conical sweep mechanism 122's motion to move the more distal portions of the manipulator to a desired position. And, conical sweep mechanism 122 may rotate a full 360 degrees or more, or its rotation may be limited to less than 360 degrees. For example, in one embodiment rotation is limited to within a range of approximately 180 degrees, between a straight up (12 o'clock) position to a straight down (6 o'clock) position. If two or more similarly configured remote center manipulators are located next to one another, then the conical sweep mechanisms 122 of each may be constrained to rotate through similar arcs to help eliminate collisions. For example, each conical sweep mechanism 122 would be constrained to rotate to a position anywhere on the arc running from 12 o'clock through 3 o'clock to 6 o'clock. In other embodiments, conical sweep mechanism 122 is provided with a gravity compensation balance feature (e.g., by using current to control motor torque as a function of mechanical load position, by using a spring to balance the mechanical load, etc.), which renders the mechanical load effectively weightless or low weight for easy hand positioning. In gravity compensation balance embodiments, a brake typically holds the manipulator in position until released, at which time a person moves the manipulator to a desired position, and then reapplies the brake to hold the manipulator at the new position.

In addition to use for set-up operations, conical sweep mechanism 122 may also be tied to the surgeon's active teleoperation control of the surgical instrument 94. Thus, conical sweep mechanism's motion may occur automatically as the result of the surgeon's control input or as the result of, for example, collision avoidance with a nearby object, such as a second manipulator, the patient, or other operating room equipment.

Figure 8:
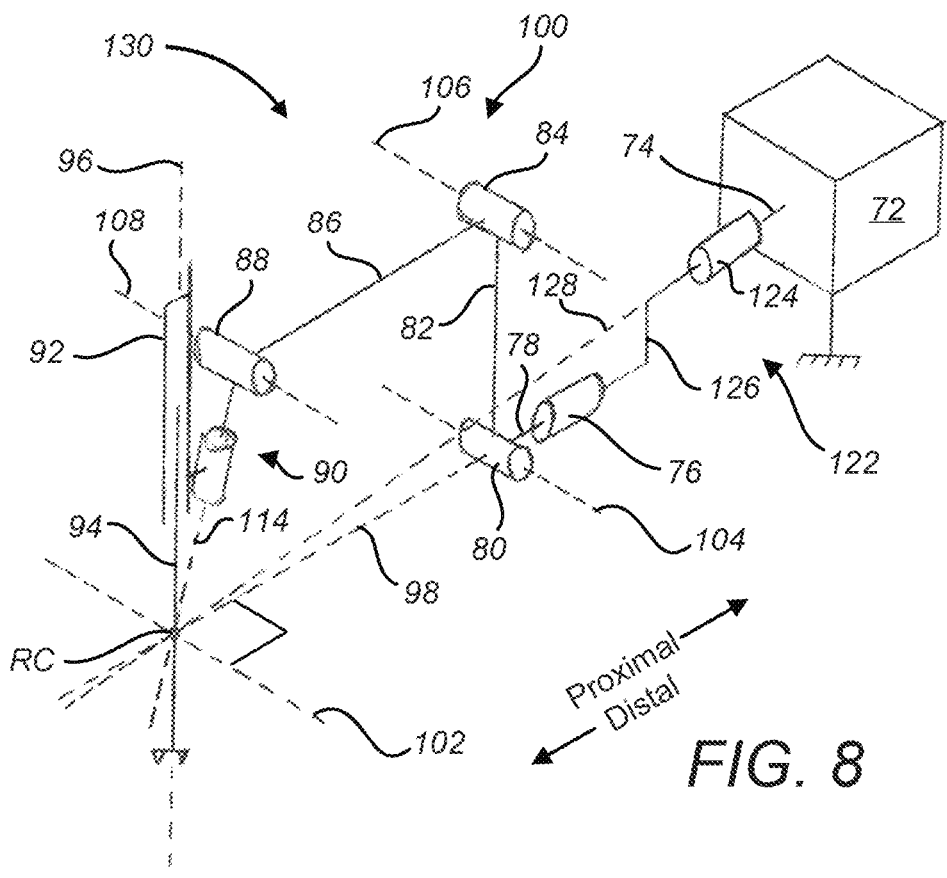
FIG. 8 is a perspective schematic representation of a remote center manipulator, in accordance with many embodiments, that includes the conical sweep joint of FIG. 6 and the conical sweep link of FIG. 7.

The various aspects of the remote center manipulators disclosed herein can be combined in any suitable fashion. For example, FIG. 8 is a perspective schematic representation of a remote center manipulator 130, in accordance with many embodiments, that includes aspects of both the remote center manipulator 70 of FIG. 6 and the remote center manipulator 120 of FIG. 7. Specifically, the remote center manipulator 130 includes the conical sweep mechanism 122, the conical sweep mechanism 90, and the parallelogram linkage portion 100. As a result, the remote center manipulator 130 has two redundant degree of freedom axes, specifically the conical sweep axis 114 and the conical sweep axis 128, about which the instrument holder 92 can be rotated around the remote center of manipulation (RC). Each of the conical sweep axis 114 and the conical sweep axis 128 is not aligned with any of the yaw axis 98, the pitch axis 102, or the insertion axis 96.

Since the remote center manipulator embodiments illustrated in FIGS. 6-8 include a yaw axis and one or more conical sweep mechanisms each with an associated conical sweep axis, and these axes of rotation are all aligned with the remote center of manipulation, the resulting redundant degrees of freedom allow the instrument shaft to remain stationary in space (i.e., in the ground reference frame associated with base 72) as the remote center manipulator is placed in various different configurations. Further, with instrument end effector roll as described above, if the end effector orientation is not aligned with insertion axis 96, then the end effector orientation also can be kept stationary in space as the remote center manipulator is placed in various configurations. Such remote center manipulators maintain a patient safety benefit of a hardware-constrained robotic surgical manipulator in which the hardware configuration prevents the remote center of manipulation from moving with reference to the patient, and such manipulators add the benefits of allowing various configurations for an individual instrument position, a feature useful in avoiding collision with adjacent manipulators, the patient, other equipment, and surgical personnel, offering increased clearance between the manipulator and patient, and offering increased access to the surgical field where the instruments enter the patient.

It should be easily recognized that if parallelogram linkage portion 100 positions insertion axis 96 not perpendicular to axis 98, then as joint 76 rotates, instrument 94 also sweeps along the surface of a cone centered on axis 96 with a vertex at the remote center of manipulation in a way similar to the instrument 94 motions as the conical sweep mechanisms rotate as described above. Thus these features provide redundant "yaw-type" degrees of freedom—arbitrarily so called because the axis of rotation intersects the remote center of manipulation. But, hardware constrained remote center manipulators in accordance with aspects of the invention are not limited to yaw-type redundant degrees of freedom.

Figure 9:
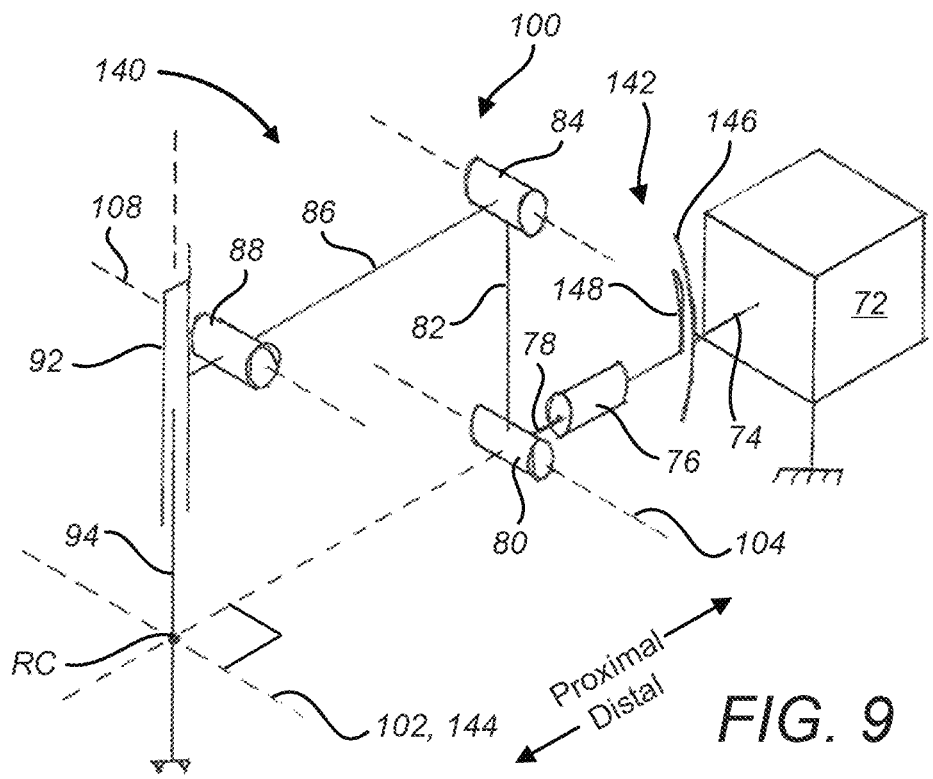
FIG. 9 is a perspective schematic representation of a remote center manipulator, in accordance with many embodiments, that includes a pitch linkage operable to reorient the outboard portion of the manipulator without moving a remote center of manipulation.

FIG. 9 is a perspective schematic representation of a remote center manipulator 140, in accordance with many embodiments. The remote center manipulator 140 includes some of the same components as the remote center manipulator 70 of FIG. 6. The shared components include the mounting base 72, the base link 74, the yaw joint 76, the extension link 78, the base parallelogram joint 80, the first parallelogram link 82, the first parallelogram joint 84, the second parallelogram link, the second parallelogram joint 88, and the instrument holder 92. The remote center manipulator 140 as depicted does not include the conical sweep mechanism 90. Instead, the second parallelogram joint 88 rotationally couples the instrument holder 92 to the second parallelogram link 86 for rotation of the instrument holder 92 relative to the second parallelogram link 86 about the second joint axis 108. The remote center manipulator 140 further includes a reorientation mechanism 142 that is operable to reorient the outboard portion of the remote center manipulator 140 about an axis 144 that intersects the remote center of manipulation (RC). The reorientation mechanism 142 includes a base 146 and a movable link 148 that is coupled with and repositionable relative to the base 146 along a curved path having a constant radius relative to the remote center of manipulation (RC), thereby limiting the corresponding motion of the instrument holder 92 to rotation about the remote center of manipulation (RC). In the embodiment shown, the axis 144 is coincident with the pitch axis 102. Therefore, as shown, parallelogram linkage portion and reorientation mechanism 142 each independently rotate instrument 94 around coincident axes 102,144 at the remote center of manipulation (RC) to provide redundant degrees of freedom. And, the hardware design of remote center manipulator 140 physically constrains instrument 94 to rotate at the remote center of manipulation (RC). Skilled artisans will understand that other mechanical structures may be used to provide the function schematically shown and described for reorientation mechanism 142. Further, one or more additional reorientation mechanisms having a function similar to reorientation mechanism 142 may be inserted in the chain between base 72 and instrument holder 92, so that remote center manipulator 140 has additional redundant degrees of freedom.

The reorientation mechanism 142 can also be configured such that the axis 144 is not aligned with (not coincident with) the pitch axis 102. For example, the reorientation mechanism 142 can be configured such that the axis 144 is aligned with the insertion axis 96 and can be configured such that the axis 144 is at any suitable angle relative to either of the pitch axis 102 and/or the insertion axis 96.

The joint associated with reorientation mechanism 142 can be powered or unpowered, and if powered can be under active surgeon control or passive control by operating room personnel. If under passive control, reorientation mechanism 142 can be used as a set-up joint prior to a surgical procedure to properly position the remote center manipulator 140 for surgery, and/or it can be used during the surgical procedure to actively reorient the outboard linkage while maintaining the position of the remote center of manipulation (RC) relative to the mounting base 72 and therefore relative to the patient and the incision at which instrument 94 enters the patient. In some passive control embodiments, a switch (e.g., on/off pushbutton, spring rocker, etc.) controls reorientation mechanism 142 movement, so that a person operates the control to move the remote center manipulator to the desired position. In other passive control embodiments, reorientation mechanism is equipped with a gravity compensation balance feature (e.g., compensation by controlling motor current depending on mechanical load position) so that the manipulator feels effectively weightless and can be easily moved by hand. For example, a brake may hold the reorientation mechanism 142 in position until released, at which point a person can easily reposition the reorientation mechanism and then reapply the brake to keep the manipulator in position.

Figure 10:
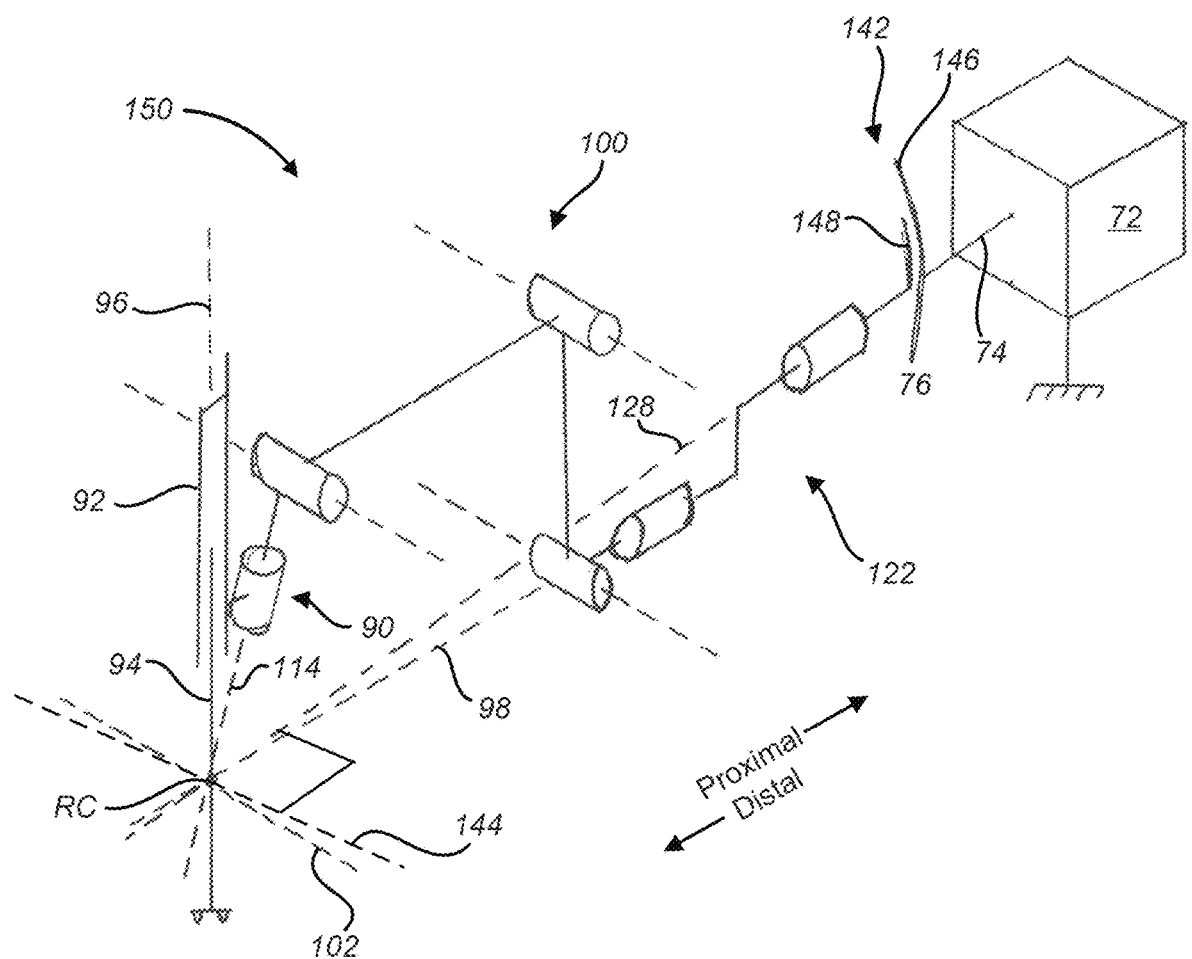
FIG. 10 is a perspective schematic representation of the a remote center manipulator, in accordance with many embodiments, that includes the conical sweep joint of FIG. 6, the conical sweep link of FIG. 7, and the pitch linkage of FIG. 9.

FIG. 10 is a perspective schematic representation of a remote center manipulator 150, in accordance with many embodiments. The remote center manipulator 150 includes aspects of both the remote center manipulator 130 of FIG. 8 and the remote center manipulator 140 of FIG. 9. Specifically, the remote center manipulator 150 includes the reorientation mechanism 142, the conical sweep mechanism 122 (which optionally may not be included), the conical sweep mechanism 90 (which optionally may not be included), and the parallelogram linkage portion 100. As a result, the remote center manipulator 150 has three redundant degrees of freedom (fewer if one of the conical sweep mechanisms is removed; more if an additional conical sweep mechanism or reorientation mechanism is added), and these degrees of freedom come from the ability to rotate around the axis 144 (driven by reorientation mechanism 142), the conical sweep axis 114 (driven by conical sweep mechanism 90), and the conical sweep axis 128 (driven by conical sweep mechanism 122). While the axis 144 is not coincident to the pitch axis 102 in the remote center manipulator 150, the axis 144 can be coincident to the pitch axis 102 in alternate embodiments.

Each of the reorientation mechanism 142 and the conical sweep mechanism 122 can be used as a set-up joint prior to a surgical procedure and/or can be used to actively reorient the outboard linkage during the surgical procedure while physically constraining the position of the remote center of manipulation (RC) relative to the mounting base 72, and therefore maintaining the position of the remote center of manipulation (RC) relative to the patient. The use of reorientation mechanism 142 as part of the set-up structure is described above, and conical sweep mechanism 122 can be similarly used.

It should be noted that the various embodiments of the remote center manipulators are each somewhat narrow so that two or more of these manipulators can be located next to one another on a surgical robot and the spacing between adjacent manipulators can be reduced to allow each manipulator to control an instrument near another instrument for effective surgical instrument placement.

Figure 11:
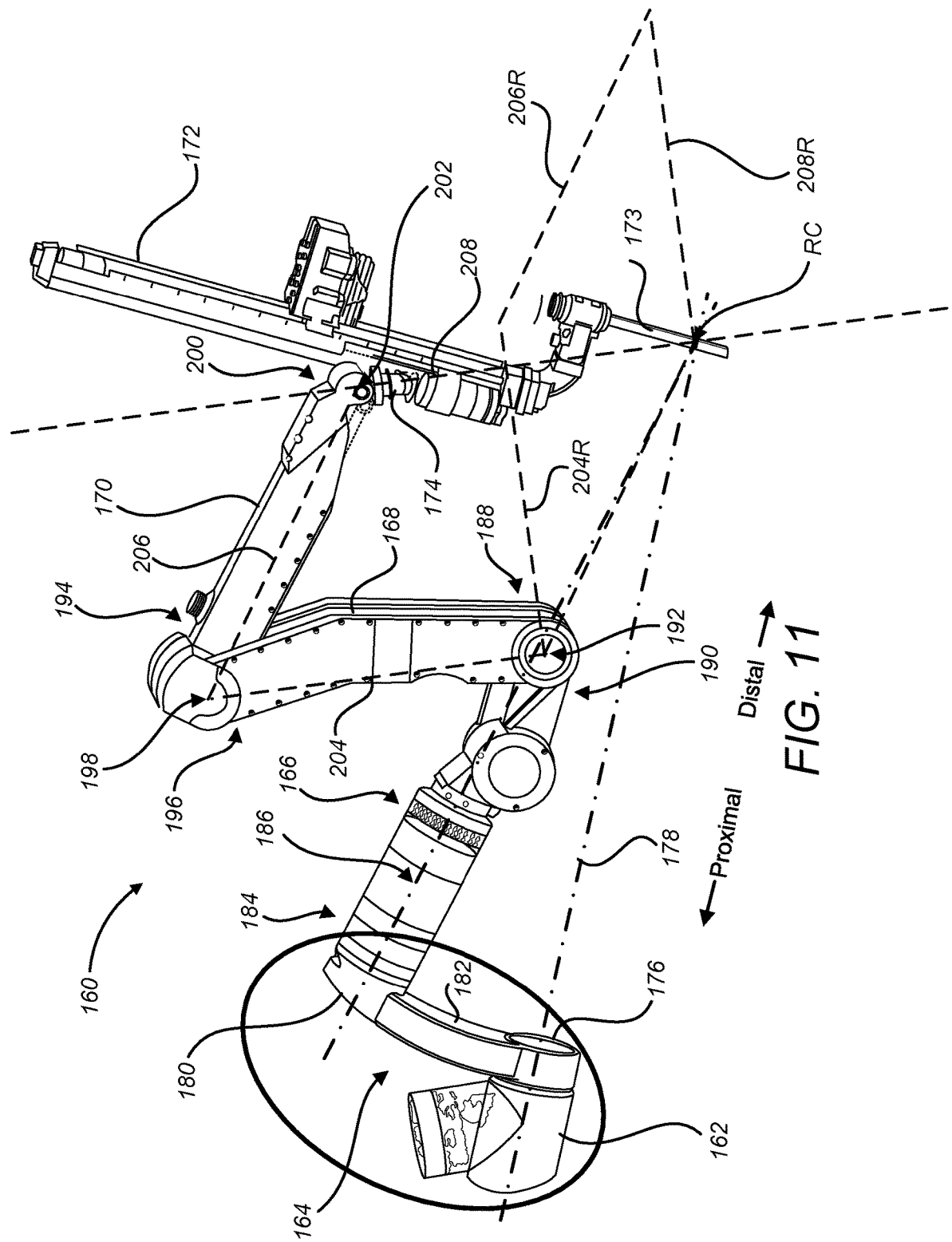
FIG. 11 shows a remote center manipulator, in accordance with many embodiments, that includes a conical sweep link operable to reorient linkage assemblies of the manipulator without moving a remote center of manipulation.

FIG. 11 shows a hardware-constrained remote center manipulator 160 in accordance with many embodiments. The manipulator 160 includes a base link 162, a conical sweep link 164, a parallelogram base link 166, a parallelogram first link 168, a parallelogram second link 170, an instrument holder 172 configured to support a detachable surgical instrument (not shown; the instrument shaft passes through the cannula 173 shown coupled at the distal end of instrument holder 172), and a conical sweep joint 174. In many embodiments, the base link 162 is held in a fixed position relative to a patient being operated on via the remote center manipulator 160. The conical sweep link 164 has a conical sweep link proximal end 176 that is mounted to the base link 162 for rotation of the conical sweep link 164 relative to the base link 162 about a first axis 178 that intersects a remote center of motion (RC) defined along the centerline of the cannula through which the instrument shaft passes. The conical sweep link 164 has a conical sweep link distal end 180 that offset from the first axis 178 and a conical sweep link body section 182 that connects the conical sweep link proximal end 176 to the conical sweep link distal end 180.

The linkage of the manipulator 160 outboard (distal) of the conical sweep link 164 is configured to provide selective movement of the instrument holder 172 that is limited to two-dimensional rotation of the instrument holder 172 about the remote center (RC) (the surgical instrument is not shown). With respect to a first direction of rotation of the instrument holder 172 about the remote center (RC), referred to herein as yaw, the parallelogram base link 166 has a proximal end 184 that is mounted to the conical sweep link distal end 180 for rotation relative to the conical sweep link distal end about a second axis 186 that also intersects the remote center (RC). By selectively rotating the parallelogram base link 166 relative to the conical sweep link distal end 180, the linkage of the manipulator 160 outboard of the parallelogram base link 166 is also selectively rotated around the second axis 186, thereby selectively rotating the instrument holder 172 around the second axis 186.

With respect to a second direction of rotation of the instrument holder 172 about the remote center (RC), referred to herein as pitch, the instrument holder 172 and the parallelogram first and second links 168, 170 are coupled so as to form a parallelogram linkage that provides movement of the instrument holder 172 that is limited to rotation about the remote center (RC) around an axis that is substantially perpendicular to the second axis 186 and to a plane of motion of the parallelogram linkage. The parallelogram first link 168 has a proximal end 188 that is rotationally coupled with a distal end 190 of the parallelogram base link 166 via a first parallelogram joint 192. The parallelogram second link 170 has a proximal end 194 that is rotationally coupled with a distal end 196 of the parallelogram first link 168 via a second parallelogram joint 198. The instrument holder 172 is coupled with a distal end 200 of the parallelogram second link 170 via a third parallelogram joint 202. The second and third parallelogram joints 198, 202 are rotationally driven by rotation of the first parallelogram joint 192 so that the first parallelogram link 168, the second parallelogram link 170, and the instrument holder 172 form the parallelogram linkage. In the position shown, the first parallelogram link 168 defines a first parallelogram side 204 extending between the first and second parallelogram joints 192, 198; the second parallelogram link 170 defines a second parallelogram side 206 extending between the second and third parallelogram joints 198, 202; and the instrument holder 172 defines a third parallelogram side 208 extending between the third parallelogram joint 202 and the remote center (RC). To illustrate the motion of the parallelogram linkage, a rotated first parallelogram side 204R is shown that represents a corresponding rotated position of the first parallelogram link 168 relative to the parallelogram base link 166, and repositioned second and third parallelogram sides 206R, 208R are shown that represent positions of the second parallelogram link 170 and the instrument holder 172, respectively, corresponding to the rotated position of the first parallelogram link 168. As illustrated, rotation of the first parallelogram link 168 relative to the parallelogram base link 166 serves to move the instrument holder 172 so that the distal end of the third parallelogram side 208 remains coincident with the remote center of manipulation (RC), thereby pitching the instrument holder 172 about an axis substantially perpendicular to the second axis 186.

The linkage of the manipulator 160 outboard of the conical sweep link 164 has an inherent singularity when the shaft of the manipulated surgical instrument lines up with the second axis 186 (yaw axis). Even when the surgical instrument shaft does not line up with the second axis 186, kinematic conditioning is poor when the angle between the surgical instrument shaft and the second axis 186 is low (e.g., 15 degrees or less). Another practical limit to extending the parallelogram linkage to the extent necessary to align the surgical instrument shaft and the second axis 186 is that the resulting length of the manipulator 160 may be undesirably long for use in the operating room environment.

To address the foregoing issues, the motion of the parallelogram linkage can be limited, for example, such that the angle of the surgical instrument shaft relative to the second axis 186 is constrained to be at least equal to a suitable angle (e.g., approximately 15 degrees). With such an angle limit, however, for any particular position and orientation of the second axis 186 there is conical volume that the surgical instrument tip cannot reach. Accordingly, the conical sweep mechanism 122 provides a way of repositioning and reorienting the second axis 186 so as to place the inaccessible conical volume to a place in the patient that the surgeon is not interested in working on. The conical sweep mechanism 122 can also be used in to rotate the instrument holder 172 around the first axis 178 as an alternative to rotation of the instrument holder 172 around the second axis 186.

A redundant axis and associated redundant degree of freedom on a hardware-constrained remote center manipulator allows the manipulator to position the surgical instrument in an individual position using any one of more than one possible combinations of joint angles. The redundant axis (the axis of the joint that provides the redundant degree of freedom) can therefore be used to avoid collisions with an adjacent manipulator, patient anatomy, or equipment (such as the operating table). When the redundant axis is mechanically constrained to pass through the remote center of manipulation (RC), the redundant axis can be reoriented during surgery without risk of moving the remote center of manipulation (RC) relative to the patient.

The conical sweep joint 174 couples the distal end 200 of the second parallelogram link 170 to the instrument holder 172. The conical sweep joint 174 is operable to selectively vary the orientation of the instrument holder 172 relative to the second parallelogram link 170 about a third axis 210 that intersects the remote center (RC). The ability to change the orientation of the instrument holder 172 relative to the second parallelogram link 170 can be used to avoid interference between the instrument holder 172 and an adjacent manipulator, to avoid interference between the instrument holder 172 and the patient, and to increase the range of motion of the instrument holder 172. In the embodiment shown, the third axis 210 is coincident with the third parallelogram side 208 thereby ensuring that third parallelogram side 208 does not change in length in response to rotation of the instrument holder 172 about the third axis 210.

Figure 12:
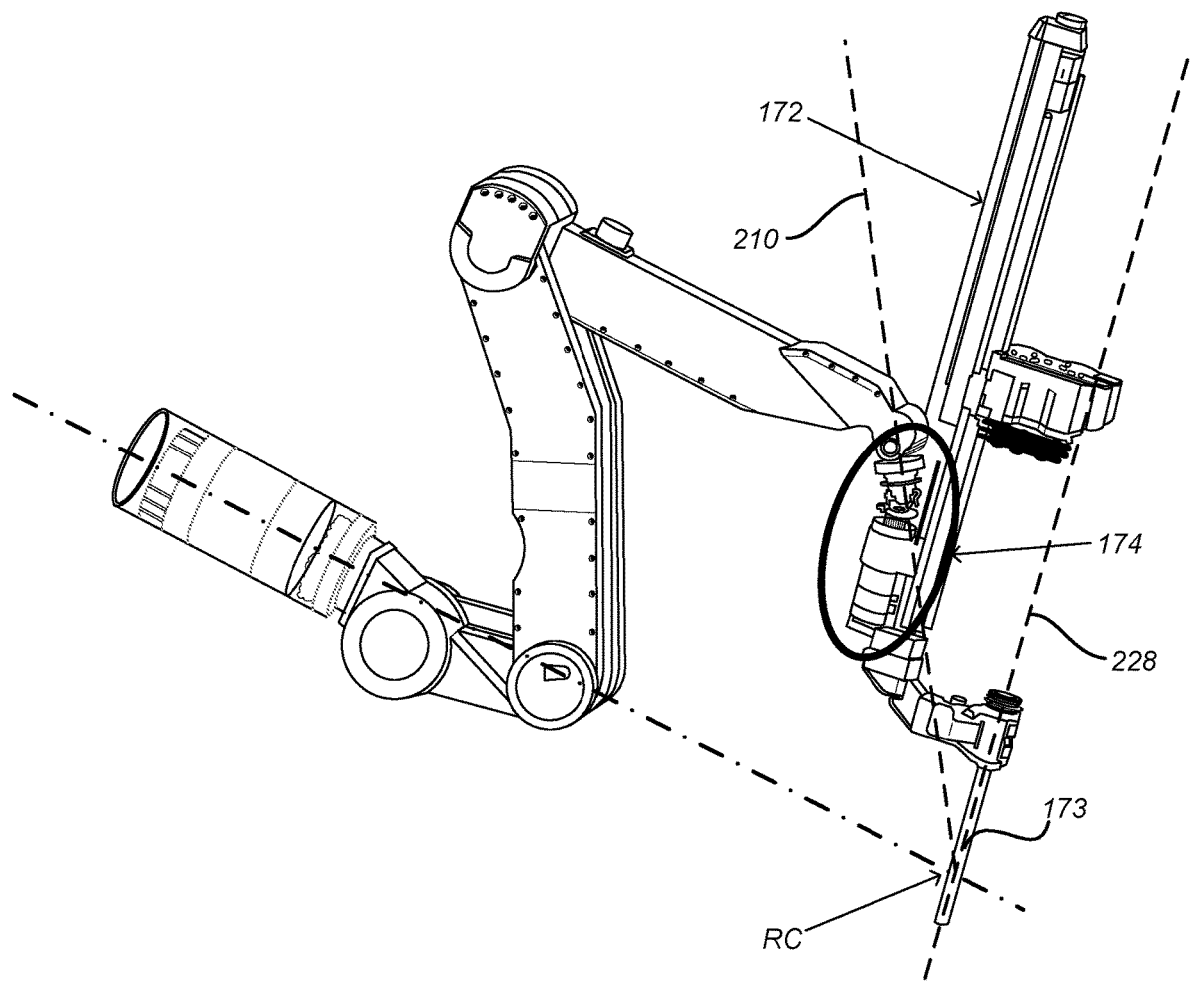
FIG. 12 shows a remote center manipulator, in accordance with many embodiments, that includes a conical sweep joint operable to reorient an instrument holder without moving a remote center of manipulation.

FIG. 12 further illustrates the conical sweep joint 174. As shown, the third axis 210 is not aligned with a centerline 228 of a surgical instrument (not shown) supported by the instrument holder 172, along which the surgical instrument is inserted and withdrawn, and around which the surgical instrument shaft rolls. The angular offset between the third axis 210 and the centerline 228 allows rotation of the conical sweep joint 174 to reorient the surgical instrument relative to the remote center (RC), thereby allowing the surgical instrument to reach different regions within the patient. And as described above, in combination the pitch motion function of the parallelogram mechanism, rotation of the conical sweep joint 174 can maintain a position and orientation of the surgical instrument with reference to the remote center of motion (RC), allowing the repositioning of the instrument holder 172 to avoid interfering with an adjacent instrument holder/surgical instrument.

Figure 13A:
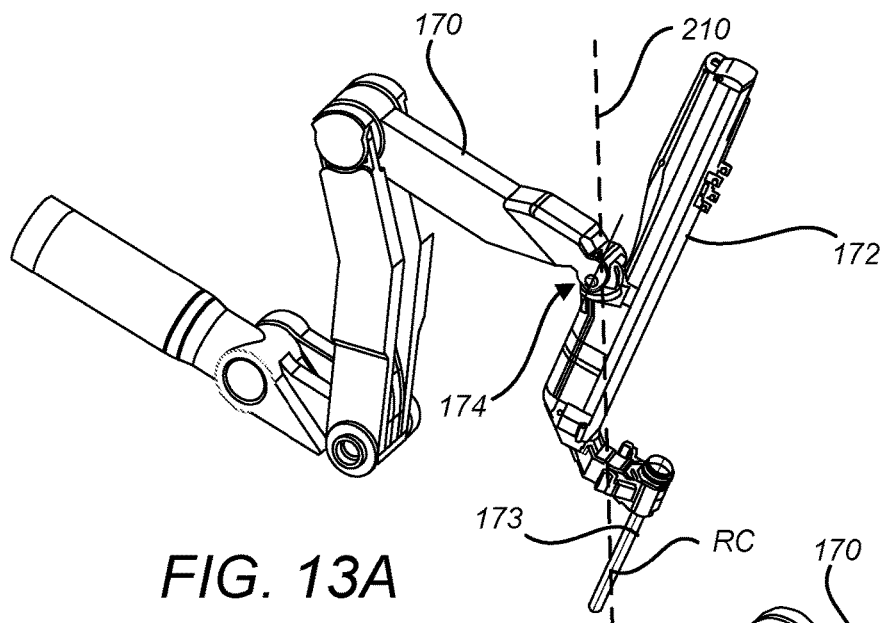
FIGS. 13A, 13B, and 13C show the remote center manipulator of FIG. 8 with the instrument holder in different orientations.
Figure 13B:
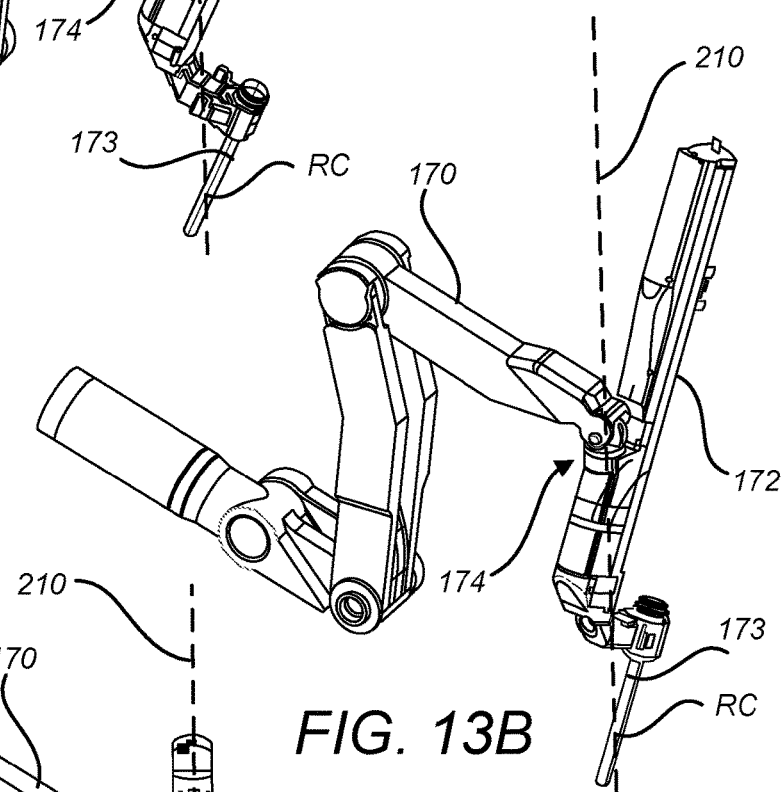
Figure 13C:
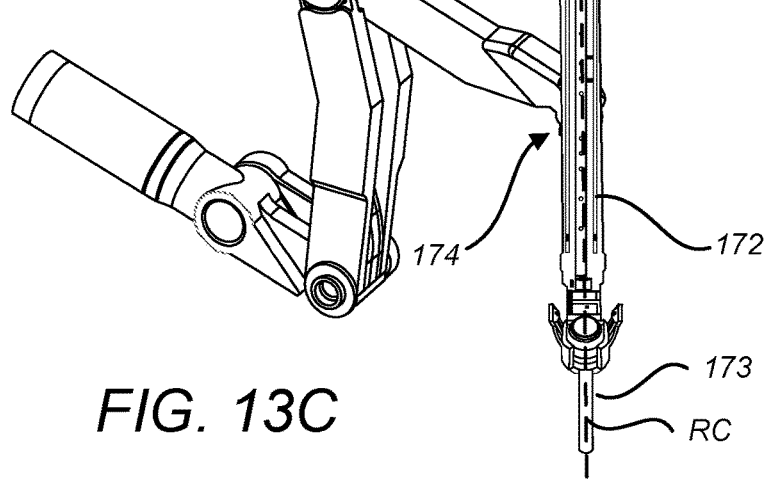

FIG. 13A, FIG. 13B, and FIG. 13C illustrate the range of motion that the conical sweep joint 174 provides. In FIG. 13A, the conical sweep joint 174 is in a centered configuration in which the instrument holder 172 is aligned with the second parallelogram link 170. In FIG. 13B, the conical sweep joint 174 is shown fully rotated in one direction, thereby orienting the instrument holder 172 in the direction shown. And in FIG. 13C, the conical sweep joint 174 is shown fully rotated in the opposite direction, thereby orienting the instrument holder 172 in the opposite direction shown. As illustrated, the different possible orientations of the instrument holder 172 provided by the conical sweep joint 174 serves to provide corresponding different insertion directions for a surgical instrument (not shown) supported by the instrument holder 172. Similarly, the redundant degree of freedom that conical sweep joint 174 provides allows a range of joint positions for the manipulator for each individual instrument position. Although not illustrated, it can be seen that the proximal conical sweep joint shown in FIG. 11 provides a similar function. And in addition, the two conical sweep joints acting together can offset the yaw joint and parallelogram mechanism to one side or the other while the instrument remains stationary. As mentioned above, rolling the end effector relative to the instrument body (e.g., rolling the end effector on the shaft, or rolling the entire shaft with the end effector attached) allows the end effector to stay stationary in space as the manipulator moves. Thus, during telesurgery the manipulator motions that exploit the advantages of the redundant degrees of freedom are transparent to the surgeon, who does not perceive any corresponding surgical end effector movement.

FIG. 14A shows a first Sine/Cosine link 228 and a second Sine/Cosine link 230 that rotationally couple some embodiments of the second parallelogram joint 198 and the third parallelogram joint 200 of the manipulator 160. The first and second Sine/Cosine links 228, 230 are so named to reflect the way the links 228, 230 are coupled to the parallelogram joints 198, 200. As illustrated at the second parallelogram joint 198, the connections between the first and second Sine/Cosine links 228, 230 and the second parallelogram joint 198 are offset by 90 degrees, with the connection between the first and second Sine/Cosine links 228, 230 and the third parallelogram joint 200 being similarly configured. While a 90-degree connection offset is preferred, other offset angles can also be used. The connection offset ensures that at least one of the links 228, 230 is always offset from a centerline 232 passing through both of the first and second parallelogram joints 198, 200, so as to always have an offset necessary to transfer torque between the second and third parallelogram joints 198, 200. By connecting each end of each of the first and second Sine/Cosine links 228, 230 to the parallelogram joints 198, 200 at the same angular orientation and radial distance, transfer or rotary motion between the second and third parallelogram joints 198, 200 can be accomplished in a positive and smooth manner.

In many embodiments, the length of the first and second Sine/Cosine links 228, 230 is adjustable to better match the length between coupling points with the second and third parallelogram joints 198, 200. Because the linkage is kinematically over-constrained, geometric deviations in the mechanical components such as lengths, angles, or operating radii may result in the development of high forces and/or a force fight in some or all of the components. The first Sine/Cosine link 228 includes a first link proximal portion 234 and a first link distal portion 236, which are fastened together at a first link joint 238. Likewise, the second Sine/Cosine link 230 includes a second link proximal portion 240 and a second link distal portion 242, which are fastened together at a second link joint 244. The first link and second link joints 238, 244 are configured such that the length of each of the first and second Sine/Cosine links 228, 230 can be varied to match the specific length of the second parallelogram link 170 on which they are installed. For example, the first link proximal portion 234 and the first link distal portion 236 can first be connected to the second parallelogram joint 198 and to the third parallelogram joint 200, respectively, and then coupled to each other via the first link joint 238 to match the specific length of the second parallelogram link 170 in which they are installed.

FIG. 14B shows a third Sine/Cosine link 246 and a fourth Sine/Cosine link 248 that rotationally couple the first parallelogram joint 192 and the second parallelogram joint 198 of the manipulator 160. The third and fourth Sine/Cosine links 246, 248 are configured and connected to the parallelogram joints 192, 198 similar to the first and second Sine/Cosine links 228, 230, so the same description applies and will not be repeated here. FIG. 14B illustrates oriented flexures 250, 252, which are configured to reduce operational force-fight levels in the third and fourth Sine/Cosine links 246, 248 (and can also be used to reduce operational force-fight levels in the first and second Sine/Cosine links 228, 230). Each of the oriented flexures 250, 252 are configured as cantilevered beams that have a stiff orientation in which the oriented flexure is aligned with the attached Sine/Cosine link (as shown at the connection of the fourth Sine/Cosine link 248 to the second parallelogram joint 198) and a compliant orientation in which the oriented flexure is oriented perpendicular with the attached Sine/Cosine link (as shown in the connection of the third Sine/Cosine link 246 to the first parallelogram joint 192). The oriented flexures 250, 252 are configured such that the stiffness of the load path provided is maximized when the attached Sine/Cosine link provides maximum mechanical advantage for the transfer of torque and the stiffness of the load path provided is minimized when the attached Sine/Cosine link provides minimum mechanical advantage for the transfer of torque.

The use of Sine/Cosine links as illustrated in FIGS. 14A and 14B is optional, and as described above other well-known ways (e.g., gears, belts, etc.) exist to couple the parallelogram links so that the parallelogram mechanism functions properly.

Figure 15:
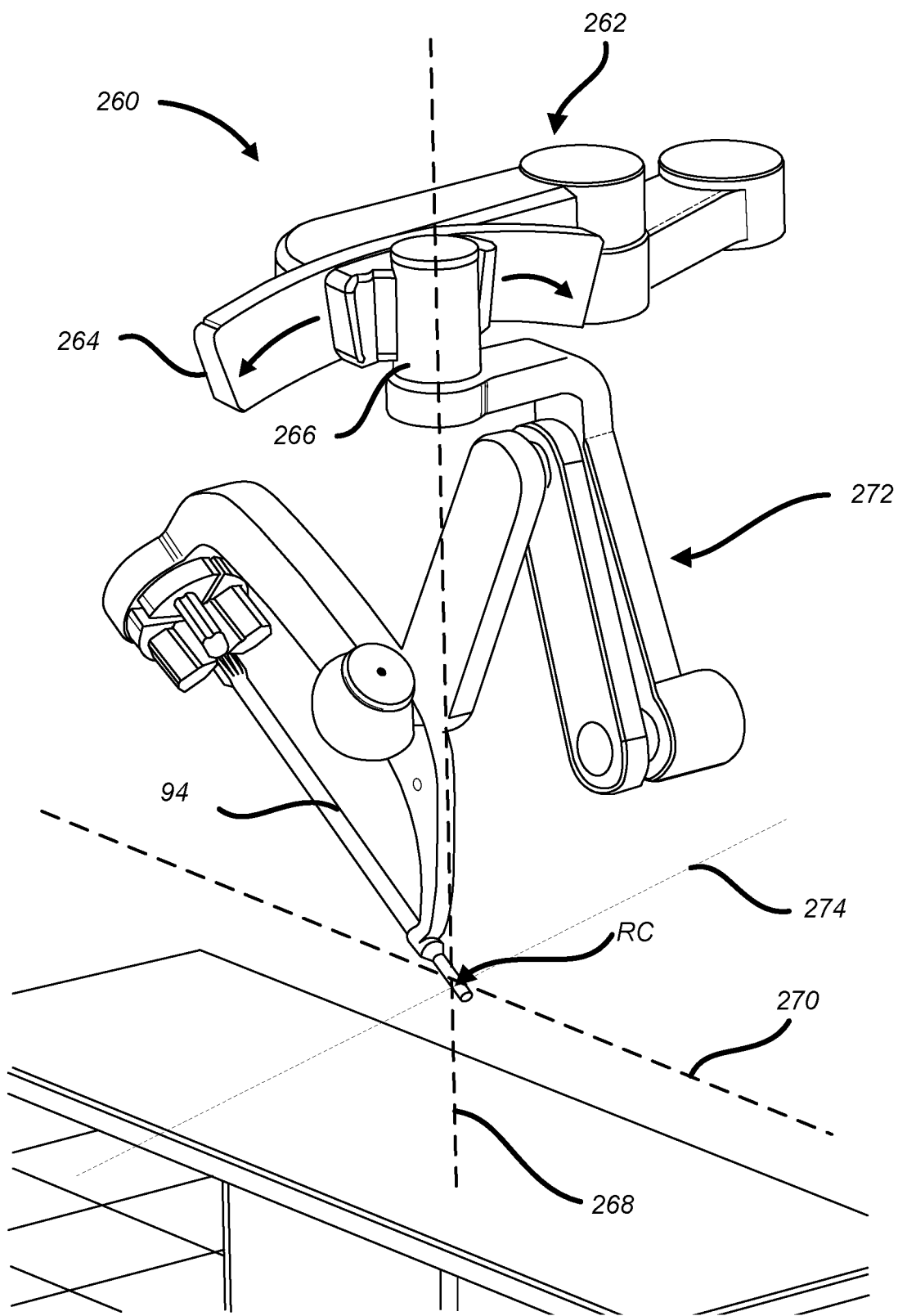
FIG. 15 shows a remote center manipulator, in accordance with many embodiments, that includes a curved feature having a constant radius of curvature relative to the remote center of manipulation and along which a base link of the outboard linkage can be repositioned.

FIG. 15 illustrates another approach for the implementation of a redundant axis that passes through the remote center of manipulation (RC) and the associated redundant mechanical degree of freedom. FIG. 15 shows a remote center manipulator 260, in accordance with many embodiments, that includes a mounting base 262 that includes a curved feature 264 having a constant radius of curvature relative to the remote center of manipulation (RC) and along which a base link 266 of the outboard (proximal) linkage of the manipulator 260 can be repositioned. The outboard linkage is mounted to the base link 266, which includes a "yaw" joint feature, for rotation about a first axis 268 that intersects the remote center of manipulation (RC). The base link 266 is interfaced with the curved feature 264 such that the base link 266 is constrained to be selectively repositioned along the curved feature 264, thereby maintaining the position of the remote center of manipulation (RC) relative to the mounting base 262, which is held in a fixed position relative to the patient. The curved feature 264 is configured such that movement of the base link 266 is limited to rotation about a second axis 270 that intersects the remote center of manipulation (RC). By changing the position of the base link 266 along the curved feature 264, the orientation of the outboard linkage of the manipulator 260 relative to the patient can be varied, thereby providing for increased range of motion of the surgical instrument manipulated by the remote center manipulator 260. Parallelogram mechanism 272 provides rotation around axis 274. It can be seen that as the entire parallelogram mechanism rotates around axis 268, axes 270 and 274 can be made coincident. It can further be seen that the embodiment shown in FIG. 15 is similar to the configuration of the embodiment shown in FIG. 9, with parallelogram mechanisms 140 and 272 being analogous, and yaw joints 76 and 266 are analogous.

Figure 16:
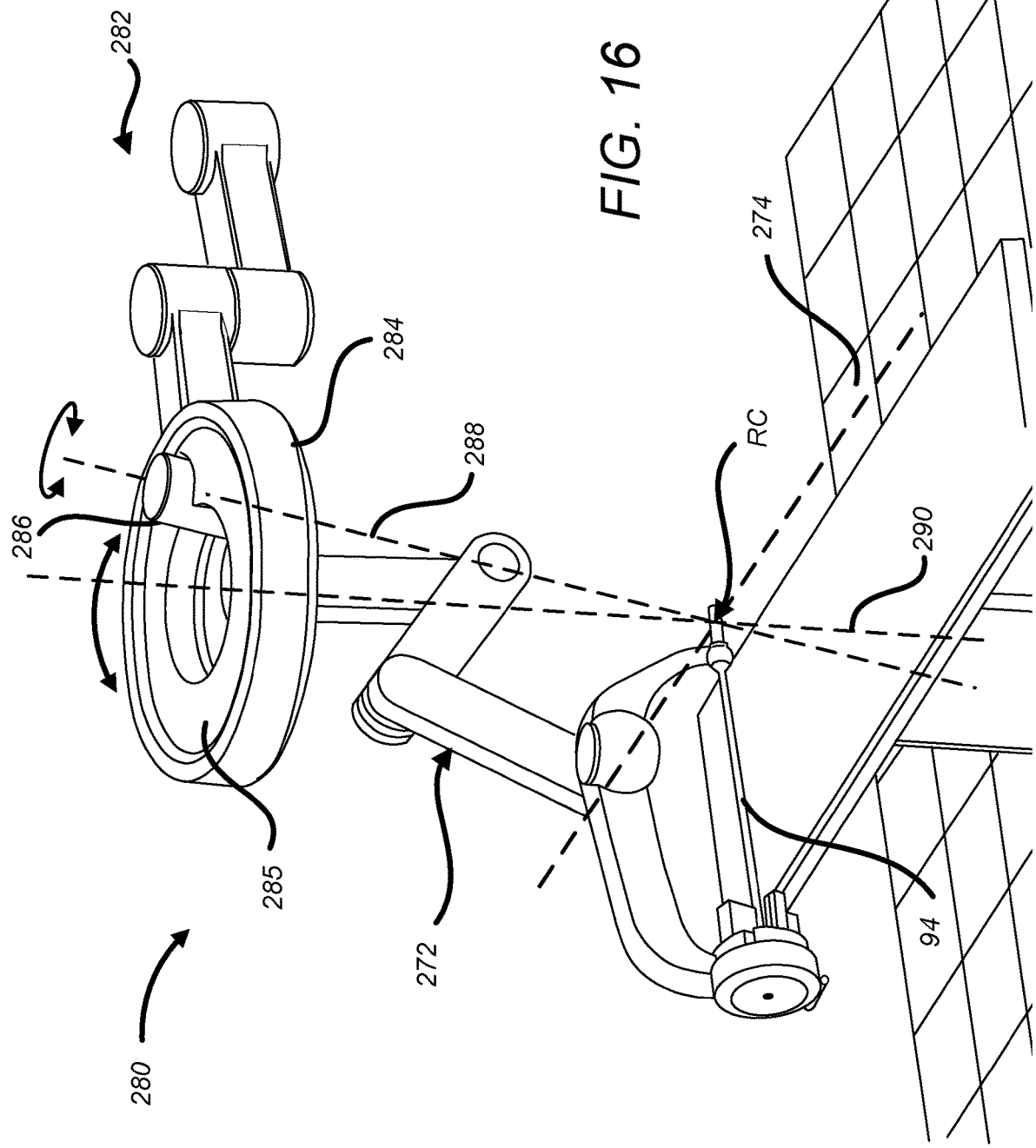
FIG. 16 shows a remote center manipulator, in accordance with many embodiments, that includes a closed-loop curved feature to which a base link of the outboard linkage is interfaced such that the base link is constrained to move along the closed-loop curved feature.

FIG. 16 illustrates another approach for the implementation of a redundant axis that passes through the remote center of manipulation (RC), providing an associated redundant degree of freedom. FIG. 16 shows a remote center manipulator 280, in accordance with many embodiments, that includes a mounting base 282 that includes a closed-loop curved feature 284 inside which a base link 286 of the outboard (distal) linkage of the manipulator 280 can be repositioned. As shown, central mount element 285 rotates inside closed-loop curved feature 284. Base link 286 is mounted on the central mount element 285 to be oriented somewhat inward toward the remote center of manipulation. The outboard linkage is mounted to the base link 286 for rotation about a first axis 288 that intersects the remote center of manipulation (RC). The closed-loop curved feature 284 is configured such that, for all positions of the base link 286 around the curved feature 284, the position of the remote center of manipulation (RC) remains fixed relative to the mounting base 282, which is held fixed relative to the patient. The closed-loop curved feature 284 is circular and is axially-symmetric about a second axis 290 that intersects the remote center of manipulation (RC). By changing the position of the base link 286 around the closed-loop curved feature 284, the orientation of the outboard linkage of the manipulator 280 relative to the patient can be varied, thereby providing for increased range of motion, arm-to-arm or arm-to-environment collision avoidance, and/or kinematic singularity avoidance for the remote center manipulator 280. A "partial circle" feature or a full circular feature where the mounting base only traverses a portion of the circle can also be used. It can be seen that curved feature 284 and its associated central mount feature 285 act as a conical sweep joint. Thus the embodiment shown in FIG. 16 is similar to the embodiment shown in FIG. 7, with conical sweep joints 122 and 284 being analogous, and yaw joints 76 and 286 being analogous.

Figure 17:
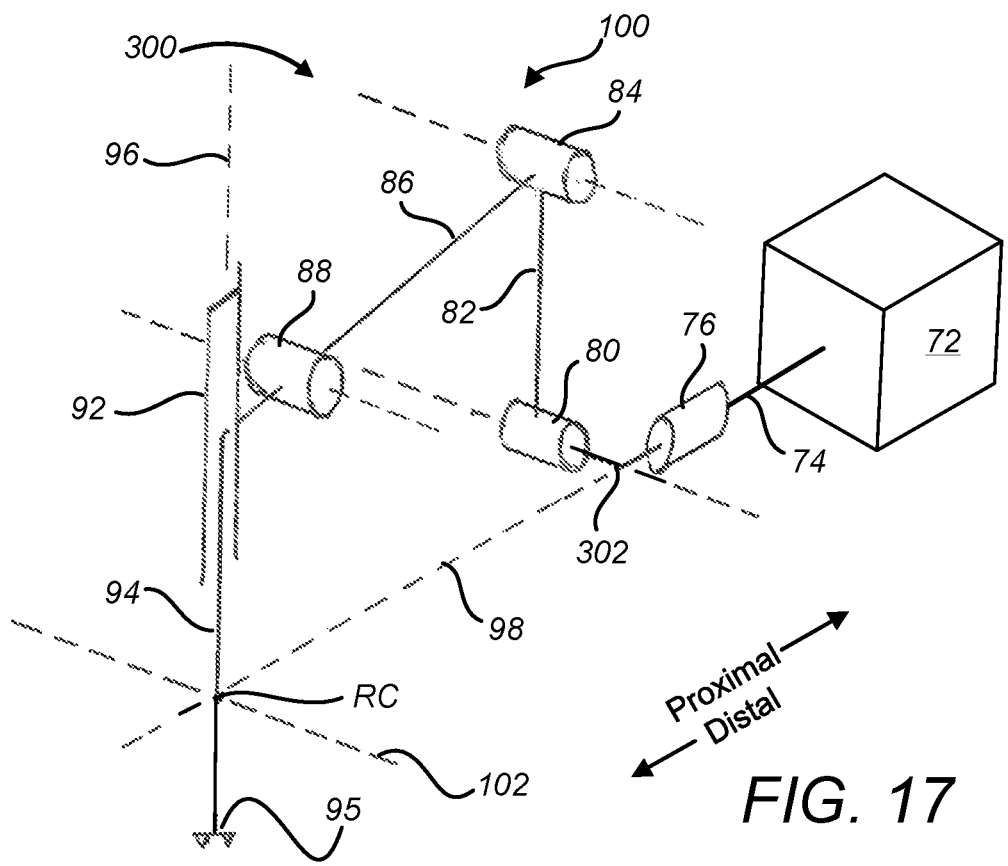
FIG. 17 is a perspective schematic representation of a remote center manipulator, in accordance with many embodiments, in which an instrument holder is rotated around a pitch axis through a remote center and rotated around a yaw axis through the remote center, the pitch axis being non-perpendicular to the yaw axis.

FIG. 17 is a perspective schematic representation of a remote center manipulator 300, in accordance with many embodiments. The remote center manipulator 300 includes some of the same components as the remote center manipulator 70 of FIG. 6. The shared components include the mounting base 72, the base link 74, the yaw joint 76, the base parallelogram joint 80, the first parallelogram link 82, the first parallelogram joint 84, the second parallelogram link 86, the second parallelogram joint 88, and the instrument holder 92. The remote center manipulator 300 can also include the conical sweep assembly 90 (not shown). The remote center manipulator 300 includes an offset extension link 302 that offsets the parallelogram linkage portion 100 from the yaw axis 98, thereby orienting the pitch axis 102 to be non-perpendicular to the yaw axis 98. Offsetting the parallelogram linkage portion 100 from the yaw axis 98 can be used to reduce the volume swept by the remote center manipulator 300 as it is rotated around the yaw axis 98 by the operation of the yaw joint 76, thereby increasing clearance to the patient and/or increasing clearance to an adjacent remote center manipulator(s). As a non-limiting example, the offset angle is 2.7 degrees in some embodiments. Although the additional clearance provided by the offset appears to be small, it can be significant during surgery, since several such manipulators are typically closely positioned to control instruments inserted into the patient. Even more significant, the increased clearance from the patient can allow an increased range of motion for the instrument end effector inside the patient, which allows surgeons to reach just a little farther if necessary to reach tissue for therapeutic purposes.

Figure 18:
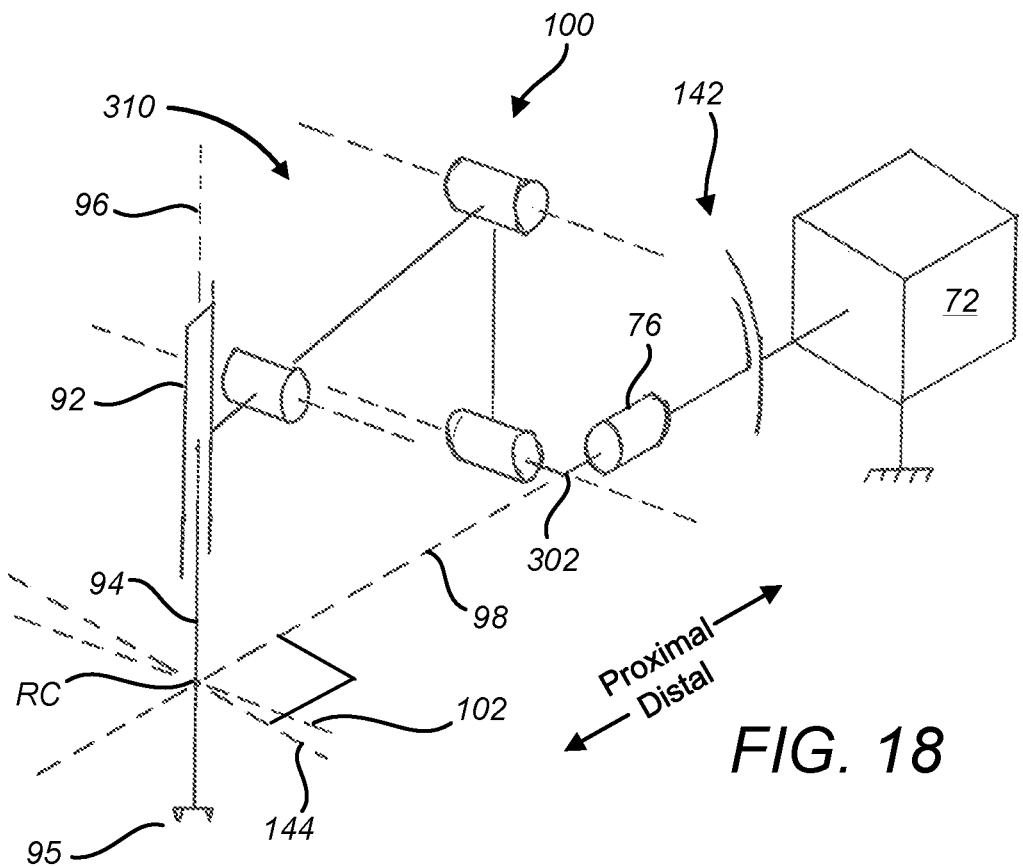
FIG. 18 is a perspective schematic representation of a remote center manipulator, in accordance with many embodiments, in which the remote center manipulator of FIG. 17 further includes the pitch linkage of FIG. 9.

FIG. 18 is a perspective schematic representation of a remote center manipulator 310, in accordance with many embodiments. The remote center manipulator 310 includes aspects of both the remote center manipulator 300 of FIG. 17 and the remote center manipulator 140 of FIG. 9. Specifically, the remote center manipulator 310 includes the reorientation mechanism 142, the offset extension link 302, and the parallelogram linkage portion 100. As a result, the remote center manipulator 310 has one redundant axis and associated degree of freedom, specifically the axis 144 (which in the embodiment shown is not aligned with the pitch axis 102) about which the instrument holder 92 can be rotated around the remote center of manipulation (RC). The reorientation mechanism 142 can be used as a set-up joint prior to a surgical procedure and/or can be used to actively reorient the outboard (distal) linkage during the surgical procedure while maintaining the position of the remote center of manipulation (RC) relative to the mounting base 72 and therefore maintaining the position of the remote center of manipulation (RC) relative to the patient.

Figure 19:
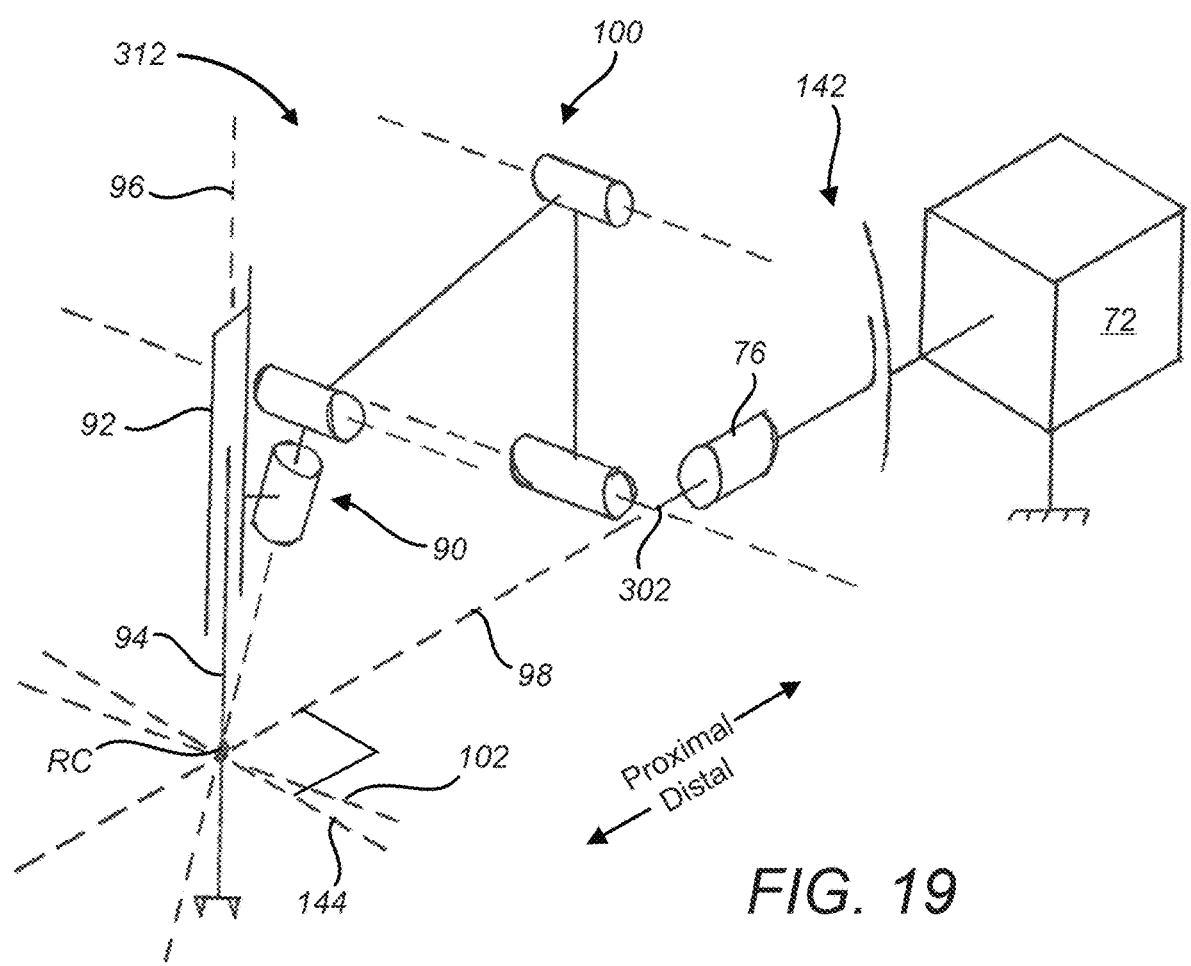
FIG. 19 is a perspective schematic representation of the remote center manipulator, in accordance with many embodiments, that in which the remote center manipulator of FIG. 18 further includes the conical sweep joint of FIG. 6.

Any suitable combination of the remote center manipulator aspects disclosed herein can be employed. For example, a remote center manipulator can include any suitable combination of the reorientation mechanism 142, the conical sweep mechanism 122, the offset extension link 302, and the conical sweep mechanism 90. FIG. 19 shows a remote center manipulator 312 that includes the reorientation mechanism 142, the offset extension link 302, the parallel linkage portion 100, and the conical sweep mechanism 90.

Figure 20:
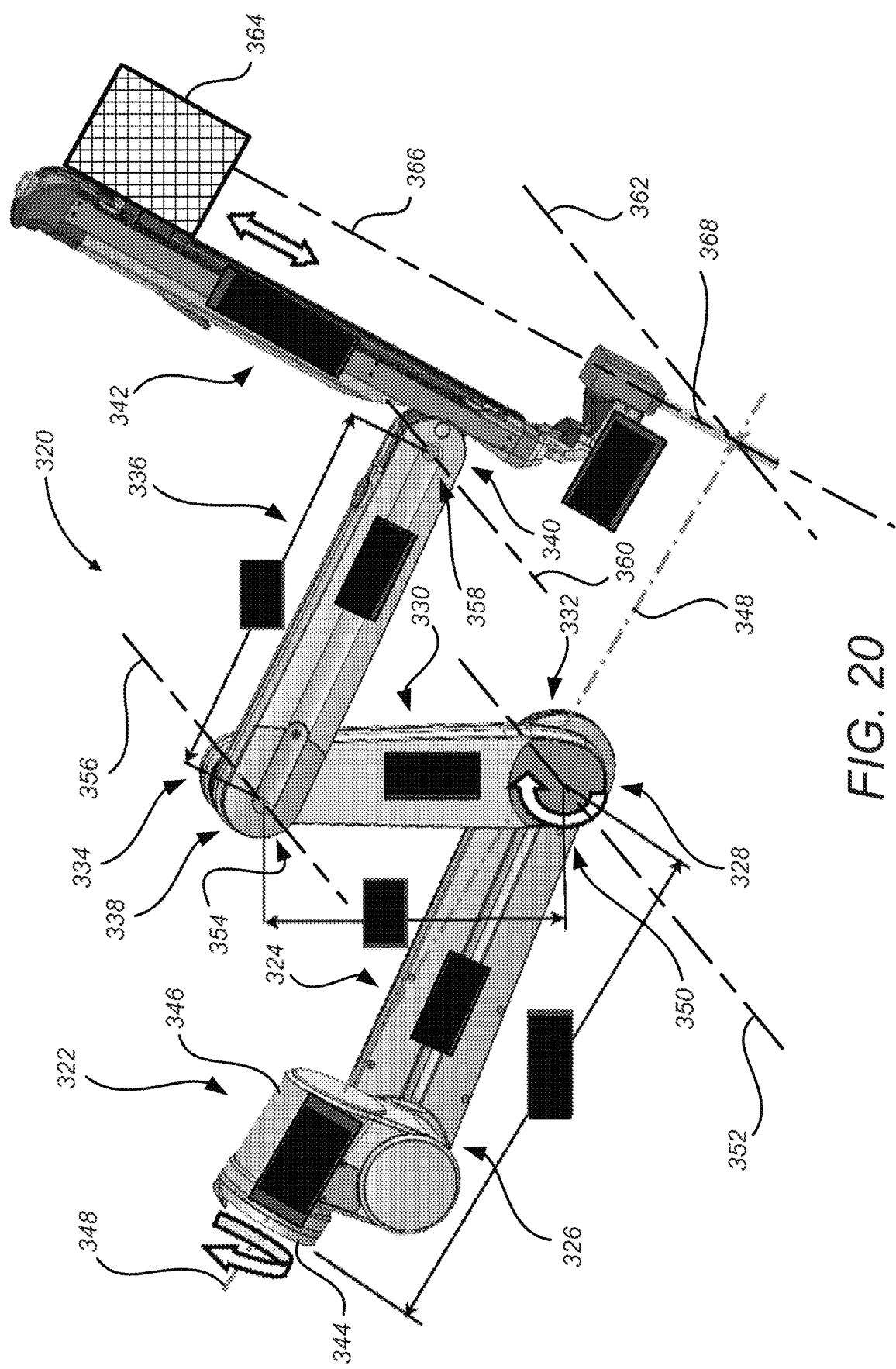
FIG. 20 is a side view of a remote center manipulator, in accordance with many embodiments.

FIG. 20 shows a remote center manipulator 320, in accordance with many embodiments. The manipulator 320 includes five units that are configured to be replaceable in the field. The five field replaceable units (FRUs) include a yaw/pitch drive assembly 322, an extension 324 having an extension proximal end 326 and an extension distal end 328, a first parallelogram link 330 having a first link proximal end 332 and a first link distal end 334, a second parallelogram link 336 having a second link proximal end 338 and a second link distal end 340, and an instrument holder 342.

The yaw/pitch drive assembly 322 includes a mounting base 344 and a yaw/pitch housing 346 that is coupled with the mounting base 344 to rotate around a yaw axis 348 that intersects a remote center of manipulation (RC) having a fixed position relative to the mounting base 344. The mounting base 344 allows the remote center manipulator 320 to be mounted and supported by set-up arms/joints of a cart mount, a ceiling mount, floor/pedestal mount, or other mounting surface. By supporting the mounting base 344 in a fixed position and orientation relative to a patient, the remote center of manipulation (RC) is held fixed relative to the patient, thereby providing an entry point for a surgical instrument held by the instrument holder 342 to be manipulated without imposing without imposing potentially dangerous forces on patient tissue at the entry location of the surgical instrument. The yaw/pitch drive assembly 322 is operable to selectively rotate the yaw/pitch housing 346 relative to the mounting base 344, thereby rotating the outboard portion of the remote center manipulator 320 such that the instrument holder 342 is rotated (yawed) around the yaw axis 348 without moving the remote center of manipulation (RC) relative to the mounting base 344.

The extension 324 provides support to a base joint 350 of a parallelogram linkage portion of the remote center manipulator 320. The extension proximal end 326 is fixedly mounted to the yaw/pitch housing 346. The first link proximal end 332 is coupled with the extension distal end 328 via the base joint 350 such that the first parallelogram link 330 rotates around a first offset pitch axis 352 relative to the extension 324. The first parallelogram link 330 is offset to a side of the extension 324 such that the first parallelogram link 330 moves in a plane of motion offset from the extension 324 and can therefore rotate into alignment and past the extension 324 without interfering with the extension 324.

The parallelogram linkage portion of the remote center manipulator 320 includes the first parallelogram link 330, the second parallelogram link 336, and the instrument holder 342. The second link proximal end 338 is coupled with the first link distal end 334 via a first intermediate joint 354 such that the second parallelogram link 336 rotates relative to the first parallelogram link 330 around a second offset pitch axis 356 that is parallel to the first offset pitch axis 352 and fixed relative to the first link distal end 334. The second parallelogram link 336 is offset to a side of the first parallelogram link 330 such that the second parallelogram link 336 moves in a plane of motion offset from the first parallelogram link 330 and can therefore rotate into alignment and past the first parallelogram link 330 without interfering with the first parallelogram link 330. The instrument holder 342 is coupled with the second link distal end 340 via a second intermediate joint 358 such that the instrument holder 342 rotates relative to the second parallelogram link 336 around a third offset pitch axis 360 that is parallel to the first offset pitch axis 352 and fixed relative to the second link distal end 340. Rotation of each of the first and second intermediate joints 354, 358 is tied to rotation of the base joint 350 such that the first parallelogram link 330, the second parallelogram link 336, and the instrument holder 342 are constrained to move as a parallelogram linkage, thereby rotating (pitching) the instrument holder about a pitch axis 362 that intersects the remote center of manipulation (RC).

The instrument holder 342 includes a carriage assembly 364 to which a surgical instrument is mounted. The instrument holder 342 includes an insertion drive mechanism operable to translate the carriage assembly 364 along an insertion axis 366, thereby controlling insertion of the surgical instrument through the remote center of manipulation (RC). The surgical instrument typically passes through a cannula 368, which is mounted at the distal end of instrument holder 342, and for which the remote center of manipulation (RC) is defined along a centerline coincident with axis 366.

Figure 21:
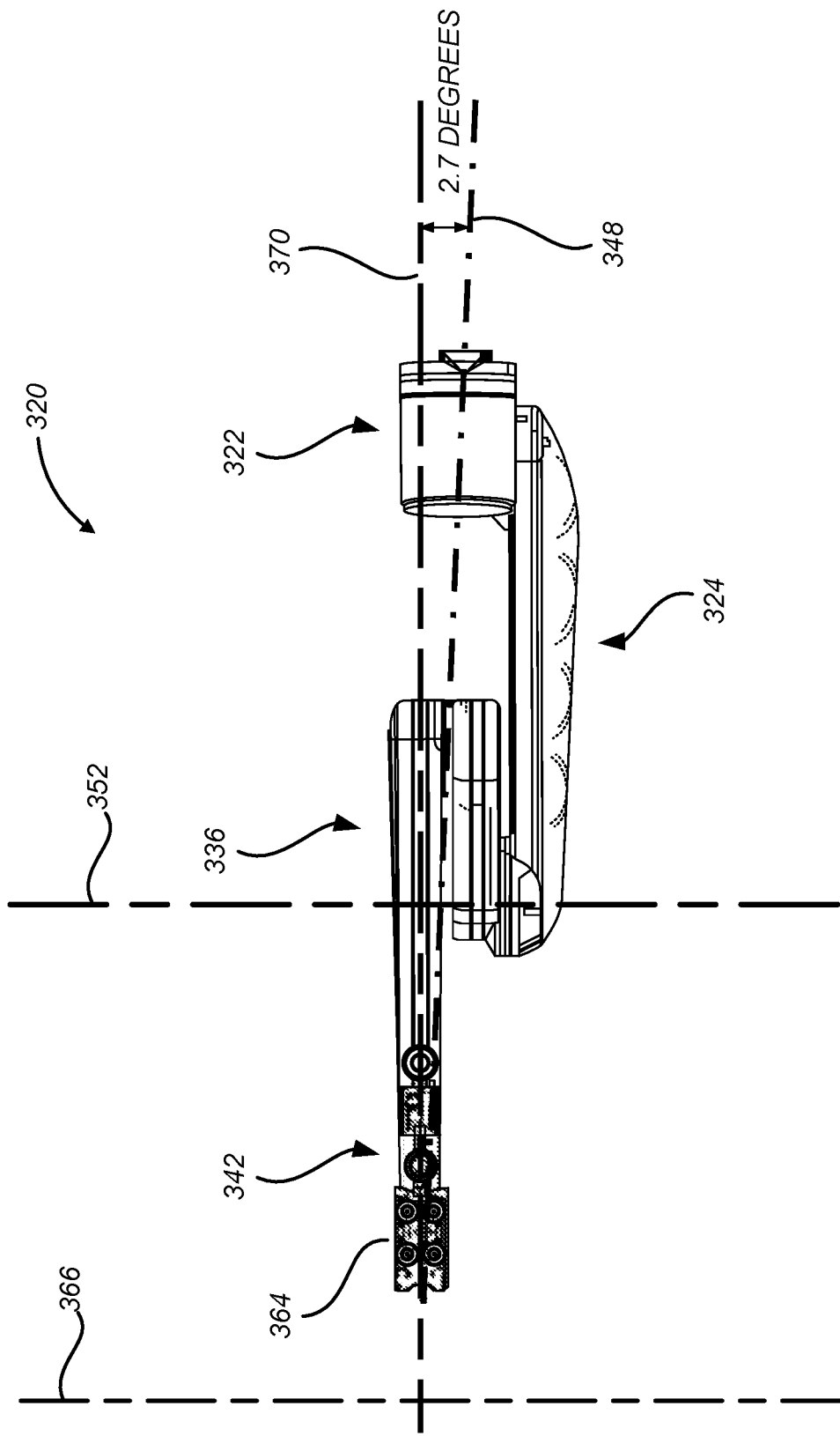
FIG. 21 is a top view of the remote center manipulator of FIG. 20.
Figure 22:
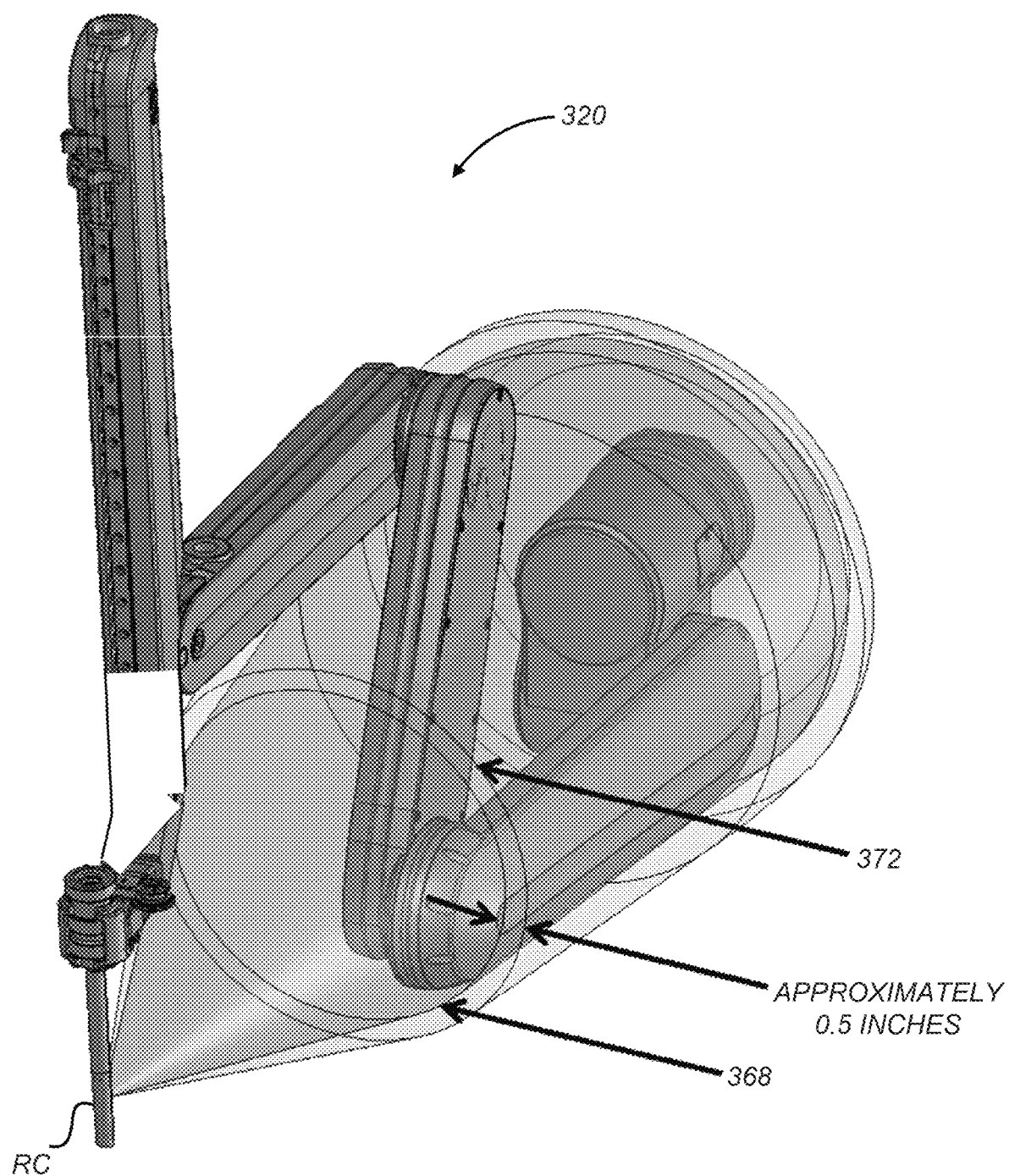
FIG. 22 illustrates a reduction in operating space envelope of the remote center manipulator of FIG. 20 achieved by skewing the pitch axis.

FIG. 21 shows a top view of the remote center manipulator 320. As shown, the yaw axis 348 and the pitch axis 366 are angularly offset by an angle other than 90 degrees. In the embodiment shown, the yaw axis 348 and the pitch axis 366 are angularly offset by 87.3 degrees. By offsetting the yaw axis 348 and the pitch axis 366 by an angle other than 90 degrees, the operating space envelope (swept volume) of the remote center manipulator 320 for rotation about the yaw axis 348 is reduced relative to the use of a 90 degree angular offset between the yaw axis 348 and the pitch axis 366. This reduction of the swept volume of the remote center manipulator 320 for rotation about the yaw axis 348 is illustrated in FIG. 22. For the embodiment shown, the angular offset of 87.3 degrees produces a relatively smaller swept volume 368 having a diameter at the base joint 350 of 7.95 inches. In comparison, when a yaw axis 370 having a 90 degree angular offset from the pitch axis 366 is used it produces a relatively larger swept volume 372 having a diameter at the base joint 350 of 8.98 inches. Accordingly, the use of the 87.3 degree angular offset produces about 0.5 inches in additional patient clearance that, as described above, can be significant for surgical performance.

Figure 23:
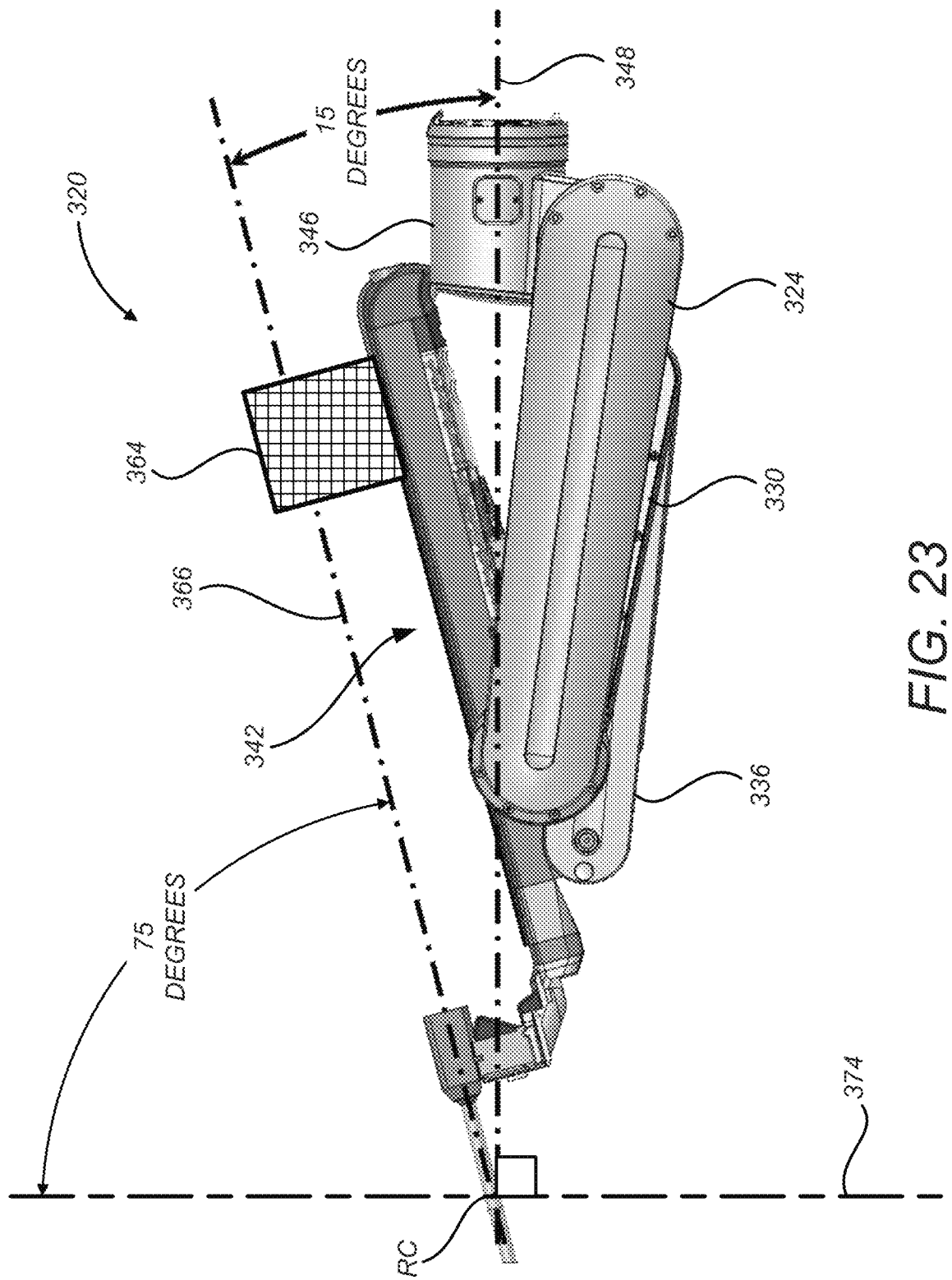
FIG. 23 is a side view of the remote center manipulator of FIG. 20 in a configuration of maximum pitch back of the instrument holder relative to the remote center of manipulation, in accordance with many embodiments.

FIG. 23 is a side view of the remote center manipulator 320 in which the instrument holder 342 is pitched back to a maximum amount. In the configuration shown, the first parallelogram link 330 has been swung to a position just past being aligned with the extension link 324 and the second parallelogram link 336 has been swung to a position just past being aligned with the first parallelogram link 330, thereby orienting the insertion axis 366 to an angular offset of 75 degrees from a perpendicular 374 to the yaw axis 348. While the remote center manipulator 320 can be configured to achieve even greater maximum pitch back angle, for example, by increasing the length of the extension link 324 such that the instrument holder 342 does not come into contact with the yaw/pitch housing 346, the additional pitch back angle gained may not be of practical value given that the kinematics of the remote center manipulator 320 with regard to yawing of the instrument holder 342 relative to the remote center of manipulation (RC) becomes increasingly poorly conditioned when the angle between the insertion axis 366 and the yaw axis 348 is reduced below 15 degrees.

Other variations are within the spirit of the present invention. Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

What is claimed is:

1. A manipulator for articulating a surgical tool during surgery, the surgical tool including an elongate shaft, the shaft having a distal working end configured for insertion into a body cavity of a patient through a remote center of manipulation, the manipulator comprising:
    an instrument holder configured to couple with the surgical tool;
    a parallelogram linkage assembly configured to produce motion of the instrument holder that is limited to rotation about a pitch axis that intersects the remote center of manipulation, the parallelogram linkage assembly comprising a base parallelogram joint;
    an offset extension link having an offset extension link distal end and an offset extension link proximal end, the offset extension link distal end being connected to the base parallelogram joint;
    a yaw joint connected to the offset extension link proximal end, the yaw joint being configured to produce motion of the instrument holder that is limited to rotation about a yaw axis that intersects the remote center of manipulation, the pitch axis being transverse to and non-perpendicular to the yaw axis, the offset extension link distal end being offset from the yaw axis; and a mounting base coupled with the yaw joint and configured to be supported in a fixed position and orientation relative to the patient.

2. The manipulator of claim 1, wherein the parallelogram linkage assembly further comprises:

a first parallelogram joint rotationally coupled with the base parallelogram joint;

a second parallelogram joint rotationally coupled with the base parallelogram joint;

a first parallelogram link having a first parallelogram link proximal end and a first parallelogram link distal end, the first parallelogram link proximal end being connected to the base parallelogram joint, the first parallelogram link distal end being connected to the first parallelogram joint; and a second parallelogram link having a second parallelogram link proximal end and a second parallelogram link distal end, the second parallelogram link proximal end being connected to the first parallelogram joint, the second parallelogram link distal end being connected to the second parallelogram joint, the second parallelogram link being connected to the instrument holder via the second parallelogram joint.

3. The manipulator of claim 1, wherein the pitch axis is non-perpendicular to the yaw axis by about 2.7 degrees.

4. The manipulator of claim 1, further comprising a reorientation mechanism configured to produce motion of the instrument holder that is limited to rotation about a reorientation axis that intersects the remote center of manipulation and is not aligned with the yaw axis, the yaw joint being connected to the mounting base via the reorientation mechanism.

5. The manipulator of claim 4, further comprising a distal conical sweep mechanism configured to produce motion of the instrument holder that is limited to rotation about a distal conical sweep axis that intersects the remote center of manipulation, the instrument holder being connected to the parallelogram linkage assembly via the distal conical sweep mechanism.

6. The manipulator of claim 1, further comprising a distal conical sweep mechanism configured to produce motion of the instrument holder that is limited to rotation about a distal conical sweep axis that intersects the remote center of manipulation, the instrument holder being connected to the parallelogram linkage assembly via the distal conical sweep mechanism.

7. The manipulator of claim 1, further comprising a proximal conical sweep mechanism configured to produce motion of the instrument holder that is limited to rotation about a proximal conical sweep axis that intersects the remote center of manipulation and is not aligned with the pitch axis or the yaw axis, the yaw joint being connected to the mounting base via the proximal conical sweep mechanism.

8. The manipulator of claim 7, further comprising a distal conical sweep mechanism configured to produce motion of the instrument holder that is limited to rotation about a distal conical sweep axis that intersects the remote center of manipulation, the instrument holder being connected to the parallelogram linkage assembly via the distal conical sweep mechanism.

9. The manipulator of claim 1, wherein the instrument holder is operable to insert the surgical tool into the patient through the remote center of manipulation and withdraw the surgical tool from the patient through the remote center of manipulation.

* * * * *